(12) United States Patent
Finn et al.

(10) Patent No.: US 7,364,750 B2
(45) Date of Patent: Apr. 29, 2008

(54) AUTOGENE NUCLEIC ACIDS ENCODING A SECRETABLE RNA POLYMERASE

(75) Inventors: John Finn, Vancouver (CA); Ian MacLachlan, Vancouver (CA)

(73) Assignee: The University of British Columbia, Vancouver, BC (CA)

( * ) Notice: Subject to any disclaimer, the term of this patent is extended or adjusted under 35 U.S.C. 154(b) by 156 days.

(21) Appl. No.: 10/136,738

(22) Filed: Apr. 30, 2002

(65) Prior Publication Data

US 2003/0108886 A1 Jun. 12, 2003

Related U.S. Application Data

(60) Provisional application No. 60/287,974, filed on Apr. 30, 2001.

(51) Int. Cl.
C12N 15/54 (2006.01)
(52) U.S. Cl. .................. 424/450; 435/194; 435/320.1; 536/23.2
(58) Field of Classification Search ............... 536/23.1, 536/24.1, 24.5; 530/300, 350; 435/462, 435/455, 411, 468, 320.1; 514/44
See application file for complete search history.

(56) References Cited

U.S. PATENT DOCUMENTS

| 4,738,927 A | 4/1988 | Taniguchi et al. |
| 6,586,410 B1 | 7/2003 | Wheeler et al. |
| 6,773,920 B1 * | 8/2004 | Dalby et al. ................ 435/462 |

FOREIGN PATENT DOCUMENTS

| WO | WO97/41243 A2 | 11/1997 |
| WO | 00/58488 A2 | 10/2000 |
| WO | WO 00/58488 A2 | 10/2000 |
| WO | WO 00/58488 A3 | 10/2000 |
| WO | WO 01/15511 A2 | 3/2001 |
| WO | WO 02/088370 A2 | 11/2002 |

OTHER PUBLICATIONS

Anderson, Nature, 1998, vol. 392: 25-30.*
Check, Erika, Feb. 13, 2003, Nature, 421: 678.*
Derossi et al. Trends Cell Bio. 1998; 8:84-87.*
Drummond et al. Nuc. Acids Res. 1985:13:7375-94.*
Elliott et al. Gene Ther. 1999; 6 :149-51.*
Juengst, ET. Jun. 2003, BMJ, 326:1410-11.*
Kmiec, American Scientist, 1999, vol. 87: 240-147.*
Schwarze et al. Trends Pharmac. Sci. 2000; 21:45-8.*
Tyagi et al. J. Biol. Chem. 2001; 276(5):3254-61.*
Verma et al., Nature, 1997, vol. 389: 239-242.*
Aints et al. J. Gene. Med. 1999; 1:275-279.*
Dietz et al. Mol. Cell. Neurosci. 2004; 27: 85-131.*
Leifert et al. Gene Ther. 2002; 9: 1422-28.*
Lindsay, MA. Curr. Opin. Pharmacol. 2002; 2: 587-94.*
Silhol et al. Eur. J. Bioch. 2002; 269: 494-501.*

Bennet, R.P. et al., "Protein delivery using VP22," Nature Biotechnology, Jan. 2002, p. 20, vol. 20.
Brisson, M. et al., "A novel T7 RNA polymerase autogene for efficient cytoplasmic expression of target genes," Gene Therapy, 1999, pp. 263-270, vol. 6.
Chen, X. et al., "A self-initiating eukaryotic transient gene expression system based on contranslection of bacteriophage T7 RNA polymerase and DNA vectors containing an T7 autophage," Nucleic Acids Research, 1994, pp. 2114-2120, vol. 22(11).
Finn, J. et al., "The development and comparison of three cytoplasmic expression systems based on the T7, T3 and SP6 phage RNA polymerase proteins," ASGT Fourth Annual Meeting, May 30-Jun. 3, 2001, Seattle, Washington.
Gao, X. and Huang, L., "Cytoplasmic expression of a reporter gene by co-delivery of T7 RNA polymerase and T7 promoter sequence with cationic liposomes," Nucleic Acids Research, 1993, pp. 2867-2872, vol. 21(12).
Derossi et al., "Trojan peptides: the penetratin system for intracellular delivery", Trends on Cell Biology 8:2: 84-87, XP-002122131 (1998).
Elroy-Stein et al., "Cytoplasmic expression system based on constitutive synthesis of bacteriophage T7 RNA polymerase in mammalian cells", Proceedings of the National Academy of Science 87:17: 6743-6747, XP-000563742 (1990).
Lindren et al., "Cell-penetrating peptides", Trends in Pharmacological Sciences 21:3: 99-103, XP-004202572 (2000).
Finn, J., et al., "An enhanced autogene-based dual-promoter cytoplasmic expression system yields increased gene expression," Gene Therapy, 2004, vol. 11, pp. 276-283.
Li, J., et al., "Murine tyrosinase expressed by a T7 vector in bone marrow-derived dendritic progenitors effectively prevents and eradicates melanoma tumors in mice," Cancer Gene Therapy, 2000, vol. 7, No. 11, pp. 1448-1455.
Brisson, et al. "A novel T7 RNA polymerase autogene for efficient cytoplasmic expression of target genes", Gene Therapy, 1999, vol. 6, pp. 263-270.
Deng, et al. "Self-amplifying expression from the T7 promoter in 3T3 mouse fibroblasts," Gene, 1994, vol. 143, pp. 245-249.
Mandel, et al. "Midbrain injection of recombinant adeno-associated virus encoding rat glial cell line-derived neurotrophic facor protects nigral neurons in a progressive 6-hydroxydopamin-induced degeneration model of Parkinson's disease in rats," Proc. Natl. Acad. Sci., 1997, vol. 94, pp. 14083-14088.
Mizuguchi, et al. "IRES-Dependent Second Gene Expression in Significantly Lower than Cap-Dependent Fisrt Gene Expression in a Bicistronic Vector," Molecular Therap, vol. 1, No. 4, pp. 376-382., Apr. 2000.
Rusnati, et al. "Interaction HIV-1 Tat Protein with Heparin," The Journal of Biological Chemistry, 1997, vol. 272, No. 17, pp. 11313-11320.
Office Action dated Mar. 7, 2006 issued in related U.S. Appl. No. 10/688,299, filed Oct. 16, 2003.
Office Action dated Nov. 6, 2006 issued in related U.S. Appl. No. 10/688,299, filed Oct. 16, 2003.

* cited by examiner

Primary Examiner—James Ketter
(74) Attorney, Agent, or Firm—Townsend and Townsend and Crew LLP

(57) ABSTRACT

This invention provides methods, nucleic acids, compounds, and compositions for expressing a product of interest in a cell that involve a secretable RNA Polymerase.

30 Claims, 7 Drawing Sheets

SEQUENCE LISTING

<160> NUMBER OF SEQ ID NOS: 47

<210> SEQ ID NO 1
<211> LENGTH: 11
<212> TYPE: PRT
<213> ORGANISM: Artificial Sequence
<220> FEATURE:
<223> OTHER INFORMATION: HIV-Tat secretion domain

<400> SEQUENCE: 1

Tyr Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 2

Tyr Ala Arg Lys Ala Arg Arg Gln Ala Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 3

Tyr Ala Arg Ala Ala Ala Arg Gln Ala Arg Ala
1               5                   10

<210> SEQ ID NO 4
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 4

Tyr Ala Arg Ala Ala Arg Ala Ala Arg Arg Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 5

Tyr Ala Arg Ala Ala Arg Ala Ala Arg Arg Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 6

Tyr Ala Arg Arg Arg Arg Arg Arg Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 7

Tyr Ala Ala Ala Ala Arg Arg Arg Arg Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: HIV-Tat variant secretion domain

<400> SEQUENCE: 8

Ala Gly Arg Lys Lys Arg Arg Gln Arg Arg
1               5                   10

<210> SEQ ID NO 9
<211> LENGTH: 34
<212> TYPE: PRT
<213> ORGANISM: Artificial Sequence
<220> FEATURE:
<223> OTHER INFORMATION: herpes simplex virus (HSV) VP22 secretion
      domain

<400> SEQUENCE: 9

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 10
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), Penetratin-1 secretion domain

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Antennapedia homeodomain third helix (residues
      53-43) secretion domain

<400> SEQUENCE: 11

Lys Lys Trp Lys Met Arg Arg Asn Gln Phe Trp Ile Lys Ile Gln Arg
1               5                   10                  15

<210> SEQ ID NO 12

```
<400> SEQUENCE: 12

000

<210> SEQ ID NO 13
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), Pro50 secretion domain

<400> SEQUENCE: 13

Arg Gln Ile Lys Ile Trp Phe Pro Asn Arg Arg Met Lys Trp Lys Lys
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), 3-Pro secretion domain

<400> SEQUENCE: 14

Arg Gln Pro Lys Ile Trp Phe Pro Asn Arg Arg Lys Pro Trp Lys Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), R52M/M54R secretion domain

<400> SEQUENCE: 15

Arg Gln Ile Lys Ile Trp Phe Gln Asn Met Arg Arg Lys Trp Lys Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), 7-Arg secretion domain

<400> SEQUENCE: 16

Arg Gln Ile Arg Ile Trp Phe Gln Asn Arg Arg Met Arg Trp Arg Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Antennapedia homeodomain third helix (residues
      43-58), W/R secretion domain

<400> SEQUENCE: 17

Arg Arg Trp Arg Arg Trp Trp Arg Arg Trp Trp Arg Arg Trp Arg Arg
1               5                   10                  15

<210> SEQ ID NO 18
<211> LENGTH: 16
<212> TYPE: PRT
<213> ORGANISM: Artificial Sequence
```

-continued

```
<220> FEATURE:
<223> OTHER INFORMATION: Kaposi's fibroblast growth factor (FGF) signal
      peptide sequence, truncated secretion domain

<400> SEQUENCE: 18

Ala Ala Val Ala Leu Leu Pro Ala Val Leu Ala Leu Leu Ala Pro
 1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: amino terminal secretory signal of human IL-2
      secretion domain

<400> SEQUENCE: 19

Met Tyr Arg Met Gln Leu Leu Ser Cys Ile Ala Leu Ser Leu Ala Leu
 1               5                   10                  15

Val Thr Asn Ser
            20

<210> SEQ ID NO 20
<211> LENGTH: 20
<212> TYPE: PRT
<213> ORGANISM: Artificial Sequence
<220> FEATURE:
<223> OTHER INFORMATION: IL-2-4 cytokine signal sequence secretion
      domain

<400> SEQUENCE: 20

Met Tyr Arg Met Ala Leu Leu Ser Cys Ile Ala Leu Ser Leu Ala Leu
 1               5                   10                  15

Val Thr Asn Ser
            20

<210> SEQ ID NO 21
<211> LENGTH: 302
<212> TYPE: PRT
<213> ORGANISM: Artificial Sequence
<220> FEATURE:
<223> OTHER INFORMATION: herpes simplex virus (HSV) VP22 sequence
      secretion domain

<400> SEQUENCE: 21

Met Thr Ser Arg Arg Ser Val Lys Ser Gly Lys Arg Glu Val Lys Arg
 1               5                   10                  15

Asp Glu Tyr Glu Asp Leu Tyr Tyr Thr Lys Ser Ser Gly Ile Ala Ser
            20                  25                  30

Lys Asp Ser Lys Lys Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Lys Arg Thr Arg Arg Lys Val Ser Gly Ala Val Leu Ser Gly Lys
                85                  90                  95

Gly Lys Ala Arg Ala Lys Lys Lys Ala Gly Ser Gly Gly Ala Gly
                100                 105                 110

Arg Thr Lys Thr Thr Ala Lys Arg Ala Lys Thr Gln Arg Val Ala
            115                 120                 125

Thr Lys Ala Lys Ala Ala Lys Ala Ala Glu Thr Thr Arg Gly Arg Lys
```

-continued

```
                130                 135                 140
Ser Ala Gln Lys Glu Ser Ala Ala Leu Lys Asp Ala Lys Ala Ser Thr
145                 150                 155                 160

Ala Lys Thr Arg Ser Lys Thr Lys Ala Gln Gly Leu Ala Arg Lys Leu
                165                 170                 175

His Phe Ser Thr Ala Lys Lys Asn Lys Asp Ala Lys Trp Thr Lys Arg
                180                 185                 190

Val Ala Gly Phe Asn Lys Arg Val Phe Cys Ala Ala Val Gly Arg Leu
                195                 200                 205

Ala Ala Met His Ala Arg Met Ala Ala Val Gln Leu Trp Asp Met Ser
210                 215                 220

Arg Lys Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Lys Asp Val Val Gln Asp Val Asp Ala Ala Thr Ala
                260                 265                 270

Thr Arg Gly Arg Ser Ala Ala Ser Arg Lys Thr Glu Arg Lys Arg Ala
                275                 280                 285

Lys Ala Arg Ser Ala Ser Arg Lys Arg Lys Val Glu Ser
290                 295                 300

<210> SEQ ID NO 22
<211> LENGTH: 23
<212> TYPE: DNA
<213> ORGANISM: Artificial Sequence
<220> FEATURE:
<223> OTHER INFORMATION: T7 RNA polymerase (RNAP) phagemid promoter
      sequence

<400> SEQUENCE: 22
taatacgact cactataggg aga                                           23

<210> SEQ ID NO 23
<211> LENGTH: 23
<212> TYPE: DNA
<213> ORGANISM: Artificial Sequence
<220> FEATURE:
<223> OTHER INFORMATION: SP6 RNA polymerase (RNAP) phagemid promoter
      sequence

<400> SEQUENCE: 23
atttaggtga cactatagaa gaa                                           23

<210> SEQ ID NO 24
<211> LENGTH: 23
<212> TYPE: DNA
<213> ORGANISM: Artificial Sequence
<220> FEATURE:
<223> OTHER INFORMATION: T3 RNA polymerase (RNAP) phagemid promoter
      sequence

<400> SEQUENCE: 24
aattaaccct cactaaaggg aga                                           23

<210> SEQ ID NO 25
<211> LENGTH: 23
<212> TYPE: DNA
<213> ORGANISM: Artificial Sequence
<220> FEATURE:
<223> OTHER INFORMATION: K11 RNA polymerase (RNAP) phagemid promoter
      sequence
```

-continued

<400> SEQUENCE: 25
aattagggca cactataggg aga                                           23

<210> SEQ ID NO 26
<211> LENGTH: 24
<212> TYPE: PRT
<213> ORGANISM: Artificial Sequence
<220> FEATURE:
<223> OTHER INFORMATION: IL-4 signal sequence secretion domain

<400> SEQUENCE: 26

Met Gly Leu Thr Ser Gln Leu Leu Pro Pro Leu Phe Phe Leu Leu Ala
 1               5                  10                  15

Cys Ala Gly Asn Phe Val His Gly
            20

<210> SEQ ID NO 27
<211> LENGTH: 302
<212> TYPE: PRT
<213> ORGANISM: Artificial Sequence
<220> FEATURE:
<223> OTHER INFORMATION: herpes simplex virus (HSV) VP22 secretion
      domain

<400> SEQUENCE: 27

Met Thr Ser Arg Arg Ser Val Lys Ser Gly Pro Arg Glu Val Pro Arg
 1               5                  10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

-continued

```
Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Pro Val Glu Gly
    290                 295                 300

<210> SEQ ID NO 28
<211> LENGTH: 6
<212> TYPE: PRT
<213> ORGANISM: Artificial Sequence
<220> FEATURE:
<223> OTHER INFORMATION: artificial secretion domain

<400> SEQUENCE: 28

Arg Arg Arg Arg Gly Cys
1               5

<210> SEQ ID NO 29
<211> LENGTH: 7
<212> TYPE: PRT
<213> ORGANISM: Artificial Sequence
<220> FEATURE:
<223> OTHER INFORMATION: artificial secretion domain

<400> SEQUENCE: 29

Arg Arg Arg Arg Arg Gly Cys
1               5

<210> SEQ ID NO 30
<211> LENGTH: 8
<212> TYPE: PRT
<213> ORGANISM: Artificial Sequence
<220> FEATURE:
<223> OTHER INFORMATION: artificial secretion domain

<400> SEQUENCE: 30

Arg Arg Arg Arg Arg Arg Gly Cys
1               5

<210> SEQ ID NO 31
<211> LENGTH: 9
<212> TYPE: PRT
<213> ORGANISM: Artificial Sequence
<220> FEATURE:
<223> OTHER INFORMATION: artificial secretion domain

<400> SEQUENCE: 31

Arg Arg Arg Arg Arg Arg Arg Gly Cys
1               5

<210> SEQ ID NO 32
<211> LENGTH: 10
<212> TYPE: PRT
<213> ORGANISM: Artificial Sequence
<220> FEATURE:
<223> OTHER INFORMATION: artificial secretion domain

<400> SEQUENCE: 32

Arg Arg Arg Arg Arg Arg Arg Arg Gly Cys
1               5                   10

<210> SEQ ID NO 33
<211> LENGTH: 11
<212> TYPE: PRT
```

<213> ORGANISM: Artificial Sequence
<220> FEATURE:
<223> OTHER INFORMATION: artificial secretion domain

<400> SEQUENCE: 33

Arg Arg Arg Arg Arg Arg Arg Arg Arg Gly Cys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: artificial secretion domain

<400> SEQUENCE: 34

Arg Arg Arg Arg Arg Arg Arg Arg Arg Arg Gly Cys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: artificial secretion domain

<400> SEQUENCE: 35

Arg Arg Arg Arg Arg Arg Arg Arg Arg Arg Arg Gly Cys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: artificial secretion domain

<400> SEQUENCE: 36

Arg Arg Arg Arg Arg Arg Arg Arg Arg Arg Arg Arg Gly Cys
1               5                   10

<210> SEQ ID NO 37
<211> LENGTH: 15
<212> TYPE: PRT
<213> ORGANISM: Artificial Sequence
<220> FEATURE:
<223> OTHER INFORMATION: artificial secretion domain

<400> SEQUENCE: 37

Arg Arg Arg Arg Arg Arg Arg Arg Arg Arg Arg Arg Arg Gly Cys
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: artificial secretion domain

<400> SEQUENCE: 38

Arg Arg Arg Arg Arg Arg Arg Arg Arg Arg Arg Arg Arg Arg Gly Cys
1               5                   10                  15

<210> SEQ ID NO 39
<211> LENGTH: 17
<212> TYPE: PRT
<213> ORGANISM: Artificial Sequence

```
<220> FEATURE:
<223> OTHER INFORMATION: artificial secretion domain

<400> SEQUENCE: 39

Arg Arg Arg Arg Arg Arg Arg Arg Arg Arg Arg Arg Arg Arg Arg Gly
 1               5                   10                  15

Cys

<210> SEQ ID NO 40
<211> LENGTH: 18
<212> TYPE: PRT
<213> ORGANISM: Artificial Sequence
<220> FEATURE:
<223> OTHER INFORMATION: artificial secretion domain

<400> SEQUENCE: 40

Arg Arg Arg Arg Arg Arg Arg Arg Arg Arg Arg Arg Arg Arg Arg Arg
 1               5                   10                  15

Gly Cys

<210> SEQ ID NO 41
<211> LENGTH: 19
<212> TYPE: PRT
<213> ORGANISM: Artificial Sequence
<220> FEATURE:
<223> OTHER INFORMATION: artificial secretion domain

<400> SEQUENCE: 41

Arg Arg Arg Arg Arg Arg Arg Arg Arg Arg Arg Arg Arg Arg Arg Arg
 1               5                   10                  15

Arg Gly Cys

<210> SEQ ID NO 42
<211> LENGTH: 20
<212> TYPE: PRT
<213> ORGANISM: Artificial Sequence
<220> FEATURE:
<223> OTHER INFORMATION: artificial secretion domain

<400> SEQUENCE: 42

Arg Arg Arg Arg Arg Arg Arg Arg Arg Arg Arg Arg Arg Arg Arg Arg
 1               5                   10                  15

Arg Arg Gly Cys
         20

<210> SEQ ID NO 43
<211> LENGTH: 21
<212> TYPE: PRT
<213> ORGANISM: Artificial Sequence
<220> FEATURE:
<223> OTHER INFORMATION: artificial secretion domain

<400> SEQUENCE: 43

Arg Arg Arg Arg Arg Arg Arg Arg Arg Arg Arg Arg Arg Arg Arg Arg
 1               5                   10                  15

Arg Arg Arg Gly Cys
         20

<210> SEQ ID NO 44
<211> LENGTH: 22
<212> TYPE: PRT
<213> ORGANISM: Artificial Sequence
<220> FEATURE:
<223> OTHER INFORMATION: artificial secretion domain
```

```
<400> SEQUENCE: 44

Arg Arg Arg Arg Arg Arg Arg Arg Arg Arg Arg Arg Arg Arg Arg
1               5                   10                  15

Arg Arg Arg Arg Gly Cys
            20

<210> SEQ ID NO 45
<211> LENGTH: 22
<212> TYPE: PRT
<213> ORGANISM: Artificial Sequence
<220> FEATURE:
<223> OTHER INFORMATION: Kaposi's fibroblast growth factor (FGF) signal
      peptide sequence - full length secretion domain

<400> SEQUENCE: 45

Met Ser Gly Asp Gly Thr Ala Ala Val Ala Leu Leu Pro Ala Val Leu
1               5                   10                  15

Leu Ala Leu Leu Ala Pro
            20

<210> SEQ ID NO 46
<211> LENGTH: 9
<212> TYPE: PRT
<213> ORGANISM: Artificial Sequence
<220> FEATURE:
<223> OTHER INFORMATION: histidine tagged Tat domain

<400> SEQUENCE: 46

Arg Lys Lys Arg Arg Gln Arg Arg Arg
1               5

<210> SEQ ID NO 47
<211> LENGTH: 7
<212> TYPE: PRT
<213> ORGANISM: Artificial Sequence
<220> FEATURE:
<223> OTHER INFORMATION: short turn-forming heptapeptide

<400> SEQUENCE: 47

Gly Gly Gly Pro Gly Lys Arg
1               5
```

AUTOGENE NUCLEIC ACIDS ENCODING A SECRETABLE RNA POLYMERASE

CROSS-REFERENCES TO RELATED APPLICATIONS

This application claims the benefit of U.S. patent application Ser. No. 60/287,974, filed Apr. 30, 2001, which is hereby incorporated by reference in its entirety for all purposes.

BACKGROUND OF THE INVENTION

Recombinant DNA methods permit the construction of nucleic acid eukaryotic expression cassettes encoding a product of interest. These expression cassettes are then introduced into the cytoplasm of eukaryotic cells using methods known in the art. However, a major difficulty in the expression of these expression cassettes is that the nucleic acid encoding the product of interest must be exported into the nucleus where the eukaryotic transcription machinery resides. Those expression cassettes that remain in the cytoplasm are not transcribed due to the lack of a cytoplasmic RNA polymerase that can transcribe the cassette.

One strategy to increase levels of expression of the product of interest from expression cassettes following non-viral cell transfection involves the use of a cytoplasmic expression system (Gao and Huang (1993) *Nucleic Acids Res.* 21: 2867-2872). The advantage of such a system is that it bypasses the need for nuclear delivery of plasmid DNA, a major obstacle in present day expression systems and in gene therapy. The efficiency of nuclear delivery following intracellular delivery is very low and is dependent on the size of the plasmid DNA molecule (Hagstrom et al. (1997) *J Cell Sci.* 110: 2323-2331). The addition of nuclear localization signals to plasmid DNA, has been shown to enhance transfection, but with limited success (Arohsohn and Hughes (1998) *J. Drug Targeting* 5: 163-169). The primary barrier to nuclear delivery of plasmid DNA is thought to be the nuclear membrane as plasmid DNA enters the nucleus more efficiently in mitotic or dividing cells, during the breakdown of the nuclear envelope (Coonrod et al. (1997) *Gene Ther.* 4: 1313-1321). As a result, gene expression following transfection is much higher in dividing than non-dividing cells (Vitadelo et al. (1994) *Hum. Gen. Ther.* 5: 11-18; Miller et al., (1992) *Mol. Cell. Biol.* 10: 4239-4242). A further limitation of nuclear expression systems is the finite, saturable limit to the amount of DNA that can be taken up by the nucleus under any condition (Brisson et al. (1999) *Human Gene Therapy* 10: 2601-2613).

Attempts have been made to incorporate non-host RNA polymerase promoters and genes encoding RNA polymerases with expression systems to overcome the above limitations. More particularly, these limitations have led to the development of strategies that do not require nuclear localization of DNA. One of these involves the use of bacteriophage T7 RNA polymerase (T7 RNAP). T7 RNAP is a single polypeptide enzyme that mediates transcription in the cytoplasm with high promoter specificity and efficiency (Davanloo et al. (1984) *Proc. Natl. Acad. Sci., U.S.A.* 81: 2035-2039). These properties have facilitated the development of a T7 based cytoplasmic expression system. Such systems require cytoplasmic delivery of both a plasmid construct containing a gene of interest under transcriptional control of the T7 promoter and a source of the T7 polymerase. Initial studies involved co-transfection of cells with plasmids carrying T7 controlled genes and purified T7 RNAP protein. These systems were able to bypass the need for the nuclear transcription machinery and yielded high levels of gene expression (Gao and Huang (1993)). Due to the instability of the T7 RNAP protein, however, the resulting gene expression was short lived, and considerable T7 RNAP associated cytotoxicity was observed (Gao and Huang (1993)).

These studies led to the development of the T7 polymerase autogene. This system consists of a T7 RNAP gene driven by its own T7 promoter, along with a reporter gene, on different plasmids. When cells were co-transfected with these constructs and purified T7 RNAP protein, rapid and sustained levels of reporter protein were detected. The T7 autogene was able to replenish its supply of T7 RNAP, resulting in sustained gene expression (Chen et al. (1994) *Nucleic Acids Res.* 22: 2114-2120). While these autogenes are effective, the transfection cocktail is difficult to prepare and, in practice, has been shown to be cytotoxic. To overcome these problems, a dual promoter autogene was created (Brisson et al. (1999) *Gene Ther.* 6: 263-270). This construct contained a T7 RNAP gene in control of both T7 (cytoplasmic) and CMV (nuclear) promoters. This construct when taken up into the nucleus resulted in low levels of T7 RNAP being produced. The T7 RNAP produced in the nucleus in turn is able to transcribe the cytoplasmic plasmid, which is the major portion of plasmid in the cell. This in turn leads to more T7 RNAP being produced which acts to amplify the production of more T7 RNAP and the reporter gene product. Theoretically, one plasmid incorporated into the nucleus would be sufficient to activate and induce high levels of gene expression from thousands of cytoplasmic plasmids. However, this effect is limited to the cell in which the RNAP is being expressed. Other cells in which DNA is not being expressed in the nucleus, do not show the autogene effect.

Thus, a need exists in the art for nucleic acids, nucleic acid compositions, and methods that permit a RNAP to enter a cell containing cytoplasmic expression cassettes and to express the nucleic acid in the cassette that is under the control of a RNA polymerase promoter. The present invention fulfills these and other needs in the art.

SUMMARY OF THE INVENTION

The present invention provides a secretable RNA polymerase (sRNAP) containing a RNA polymerase (RNAP) linked to a secretion domain.

One embodiment of the present invention is a nucleic acid comprising a secretable RNA polymerase expression cassette. The expression cassette comprises a eukaryotic promoter and a RNA polymerase promoter operably linked to a nucleic acid encoding a secretable RNA polymerase comprising a RNA polymerase and a secretion domain; and a RNA polymerase promoter operably linked to a nucleic acid encoding a product of interest. In certain embodiments, the RNA polymerase is a non-host RNA polymerase. Examples of RNAPs that can be linked to a secretion domain include, but are not limited to, a phagemid RNA polymerase, a prokaryotic RNA polymerase, an archaebacterial RNA polymerase, a plant RNA polymerase, a fungal RNA polymerase, a eukaryotic RNA polymerase, a viral RNA polymerase, mitochondrial RNA polymerase, and a choroplast RNA polymerase. In particularly preferred embodiments, the RNAPs are selected from the group consisting of a SP6 RNA Polymerase, a T7 RNA Polymerase, a K11 RNA Polymerase, and a T3 RNA Polymerase. The secretion domains that are linked to the RNAP can be synthesized or obtained from any of a variety of different sources. For example, the secretion domains can be chosen from the following secretion domains: SEQ ID NO: 1 (HIV-Tat, Tyr-Gly-Arg-Lys-Lys-Arg-Arg-Gln-Arg-Arg-Arg); SEQ ID NO: 2 (HIV-Tat Variant, Tyr-Ala-Arg-Lys-Ala-Arg-Arg-Gln-Ala-Arg-Arg); SEQ ID NO: 3 (HIV-Tat Variant, Tyr-Ala-Arg-Ala-Ala-Ala-Arg-Gln-Ala-Arg-Ala); SEQ ID NO: 4 (HIV-Tat Variant, Tyr-Ala-Arg-Ala-Ala-Arg-Ala-Ala-Arg-Arg); SEQ ID NO: 5 (HIV-Tat Variant, Tyr-Ala-Arg-Ala-Ala-Arg-Ala-Ala-Arg-Ala); SEQ ID NO: 6 (HIV-Tat Variant, Tyr-Ala-Arg-Arg-Arg-Arg-Arg-Arg-Arg-Arg); SEQ ID NO: 7 (HIV-Tat Variant, Tyr-Ala-Ala-Ala-Ala-Arg-Arg-Arg-Arg-Arg-Arg); SEQ ID NO: 8 (HIV-Tat Variant, Ala-Gly-Arg-Lys-Lys-Arg-Arg-Gln-Arg-Arg-Arg); SEQ ID NO: 9 (HSV VP22, Asp-Ala-Ala-Thr-Ala-Thr-Arg-Gly-Arg-Ser-Ala-Ala-Ser -Arg-Pro-Thr-Glu-Arg-Pro-Arg-Ala-Pro-Ala-Arg-Ser-Ala-Ser-Arg-Pro-Arg-Arg-Pro-Val-Glu); SEQ ID NO: 10 (Antennapedia third Helix, 43-58, Penetratin-1, Arg-Gln-Ile-Lys -Ile-Trp-Phe-Gln-Asn-Arg-Arg-Met-Lys-Trp-Lys-Lys); SEQ ID NO: 11 (Antennapedia third Helix, 53-43, Lys-Lys-Trp-Lys-Met-Arg-Arg-Asn-Gln-Phe-Trp-Ile-Lys-Ile-Gln-Arg); SEQ ID NO: 12 (Antennapedia third Helix, 43-58, D-amino acids Arg-Gln-Ile-Lys -Ile-Trp-Phe-Gln-Asn-Arg-Arg-Met-Lys-Trp-Lys-Lys); SEQ ID NO: 13 (Antennapedia third Helix, 43-58, Pro50, Arg-Gln-Ile-Lys-Ile-Trp-Phe-Pro-Asn-Arg-Arg-Met-Lys-Trp-Lys-Lys); SEQ ID NO: 14 (Antennapedia third Helix, 43-58, 3-Pro, Arg-Gln-Pro-Lys -Ile-Trp-Phe-Pro-Asn-Arg-Arg-Lys-Pro-Trp-Lys-Lys); SEQ ID NO: 15 (Antennapedia third Helix, 43-58, R52M/M54R, Arg-Gln-Ile-Lys-Ile-Trp-Phe-Gln-Asn-Met-Arg-Arg-Lys-Trp-Lys-Lys); SEQ ID NO: 16 (Antennapedia third Helix, 43-58, 7-Arg, Arg-Gln -Ile-Arg-Ile-Trp-Phe-Gln-Asn-Arg-Arg-Met-Arg-Trp-Arg-Arg); SEQ ID NO: 17 (Antennapedia third Helix, 43-58, W/R, Arg-Arg-Trp-Arg-Arg-Trp-Trp-Arg-Arg-Trp -Trp-Arg-Arg-Trp-Arg-Arg); SEQ ID NO: 18 (Kaposi's FGF signal sequence, truncated Ala-Ala-Val-Ala-Leu-Leu-Pro-Ala-Val-Leu-Leu-Ala-Leu-Leu-Ala-Pro); SEQ ID NO: 19 (the amino terminal secretory signal of human IL-2; Met-Tyr-Arg-Met-Gln-Leu-Leu-Ser -Cys-Ile-Ala-Leu-Ser-Leu-Ala-Leu-Val-Thr-Asn-Ser); SEQ ID NO: 20 (cytokine signal sequence); Met-Tyr-Arg-Met-Ala-Leu-Leu-Ser-Cys-Ile-Ala-Leu-Ser-Leu-Ala-Leu-Val -Thr-Asn-Ser); and SEQ ID NO: 21 (Met-Thr-Ser-Arg-Arg-Ser-Val-Lys-Ser-Gly-Lys -Arg-Glu-Val-Lys-Arg-Asp-Glu-Tyr-Glu-Asp-Leu-Tyr-Tyr-Thr-Pro-Ser-Ser-Gly-Ile-Ala -Ser-Lys-Asp-Ser-Lys-Lys-Asp-Thr-Ser-Arg-Arg-Gly-Ala-Leu-Gln-Thr-Arg-Ser-Arg -Gln-Arg-Gly-GLu-Val-Arg-Phe-Val-Gln-Tyr-Asp-Glu-Ser-Asp-Tyr-Ala-Leu-Tyr-Gly -Gly-Ser-Ser-Ser-Glu-Asp-Asp-Glu-His-Pro-Glu-Val-Lys-Arg-Thr-Arg-Arg-Lys-Val-Ser -Gly-Ala-Val-Leu-Ser-Gly-Lys-Gly-Lys-Ala-Arg-Ala-Lys-Lys-Lys-Lys-Ala-Gly-Ser -Gly-Gly-Ala-Gly-Arg-Thr-Lys-Thr-Thr-Ala-Lys-Arg-Ala-Lys-Arg-Thr-Gln-Arg-Val -Ala-Thr-Lys-Ala-Lys-Ala-Ala-Lys-Ala-Ala-Glu-Thr-Thr-Arg-Gly-Arg-Lys-Ser-Ala -Gln-Lys-Glu-Ser-Ala-Ala-Leu-Lys-Asp-Ala-Lys-Ala-Ser-Thr-Ala-Lys-Thr-Arg-Ser-Lys -Thr-Lys-Ala-Gln-Gly-Leu-Ala-Arg-Lys-Leu-His-Phe-Ser-Thr-Ala-Lys-Lys-Asn-Lys -Asp-Ala-Lys-Trp-Thr-Lys-Arg-Val-Ala-Gly-Phe-Asn-Lys-Arg-Val-Phe-Cys-Ala-Ala -Val-Gly-Arg-Leu-Ala-Ala-Met-His-Ala-Arg-Met-Ala-Ala-Val-Gln-Leu-Trp-Asp-Met -Ser-Arg-Lys-Arg-Thr-Asp-Glu-Asp-Leu-Asn-Glu-Leu-Leu-Gly-Ile-Thr-Thr-Ile-Arg -Val-Thr-Val-Cys-Glu-Gly-Lys-Asn-Leu-Leu-Gln-Arg-Ala-Asn-Glu-Leu-Val-Asn-Lys -Asp-Val-Val-Gln-Asp-Val-Asp-Ala-Ala-Thr-Ala-Thr-Arg-Gly-Arg-Ser-Ala-Ala-Ser -Arg-Lys-Thr-Glu-Arg-Lys-Arg-Ala-Lys-Ala-Arg-Ser-Ala-Ser-Arg-Lys-Arg-Arg-Lys -Val-Glu-Ser), SEQ ID NO:26 (IL-4 signal sequence Met-Gly-Leu-Thr-Ser-Gln-Leu-Leu -Pro-Pro-Leu-Phe-Phe-Leu-Leu-Ala-Cys-Ala-Gly-Asn-Phe-Val-His-Gly), SEQ ID NO:27 (VP22 Met-Thr-Ser-Arg-Arg-Ser-Val-Lys-Ser-Gly-Pro-Arg-Glu-Val-Pro-Arg-Asp-Glu -Tyr-Glu-Asp-Leu-Tyr-Tyr-Thr-Pro-Ser-Ser-Gly-Met-Ala-Ser-Pro-Asp-Ser-Pro-Pro -Asp-Thr-Ser-Arg-Arg-Gly-Ala-Leu-Gln-Thr-Arg-Ser-Arg-Gln-Arg-Gly-Glu-Val-Arg -Phe-Val-Gln-Tyr-Asp-Glu-Ser-Asp-Tyr-Ala-Leu-Tyr-Gly-Gly-Ser-Ser-Ser-Glu-Asp -Asp-Glu-His-Pro-Glu-Val-Pro-Arg-Thr-Arg-Arg-Pro-Val-Ser-Gly-Ala-Val-Leu-Ser -Gly-Pro-Gly-Pro-Ala-Arg-Ala-Pro-Pro-Pro-Pro-Ala-Gly-Ser-Gly-Gly-Ala-Gly-Arg -Thr-Pro-Thr-Thr-Ala-Pro-Arg-Ala-Pro-Arg-Thr-Gln-Arg-Val-Ala-Thr-Lys-Ala-Pro -Ala-Ala-Pro-Ala-Ala-Glu-Thr-Thr-Arg-Gly-Arg-Lys-Ser-Ala-Gln-Pro-Glu-Ser-Ala -Ala-Leu-Pro-Asp-Ala-Pro-Ala-Ser-Thr-Ala-Pro-Thr-Arg-Ser-Lys-Thr-Pro-Ala-Gln -Gly-Leu-Ala-Arg-Lys-Leu-His-Phe-Ser-Thr-Ala-Pro-Pro-Asn-Pro-Asp-Ala-Pro-Trp -Thr-Pro-Arg-Val-Ala-Gly-Phe-Asn-Lys-Arg-Val-Phe-Cys-Ala-Ala-Val-Gly-Arg-Leu -Ala-Ala-Met-His-Ala-Arg-Met-Ala-Ala-Val-Gln-Leu-Trp-Asp-Met-Ser-Arg-Pro-Arg -Thr-Asp-Glu-Asp-Leu-Asn-Glu-Leu-Leu-Gly-Ile-Thr-Thr-Ile-Arg-Val-Thr-Val-Cys -Glu-Gly-Lys-Asn-Leu-Leu-Gln-Arg-Ala-Asn-Glu-Leu-Val-Asn-Pro-Asp-Val-Val-Gln -Asp-Val-Asp-Ala-Ala-Thr-Ala-Thr-Arg-Gly-Arg-Ser-Ala-Ala-Ser-Arg-Pro-Thr-Glu -Arg-Pro-Arg-Ala-Pro-Ala-Arg-Ser-Ala-Ser-Arg-Pro-Arg-Arg-Pro-Val-Glu-Gly), SEQ ID NO:28 (Arg-Arg-Arg-Arg-Gly-Cys), SEQ ID NO:29 (Arg-Arg-Arg-Arg-Arg -Gly-Cys), SEQ ID NO:30 (Arg-Arg-Arg-Arg-Arg-Arg-Gly-Cys), SEQ ID NO:31 (Arg -Arg-Arg-Arg-Arg-Arg-Arg-Gly-Cys), SEQ ID NO:32 (Arg-Arg-Arg-Arg-Arg-Arg-Arg -Gly-Cys), SEQ ID NO:33 (Arg-Arg-Arg-Arg-Arg-Arg-Arg-Arg-Arg-Gly-Cys), SEQ ID NO:34 (Arg-Arg-Arg-Arg-Arg-Arg-Arg-Arg-Arg-Arg-Gly-Cys), SEQ ID NO:35 (Arg-Arg-Arg-Arg-Arg-Arg-Arg-Arg-Arg-Arg-Arg-Gly-Cys), SEQ ID NO:36 (Arg-Arg -Arg-Arg-Arg-Arg-Arg-Arg-Arg-Arg-Arg-Arg-Gly-Cys), SEQ ID NO:37 (Arg-Arg-Arg -Arg-Arg-Arg-Arg-Arg-Arg-Arg-Arg-Arg-Arg-Gly-Cys), SEQ ID NO:38 (Arg-Arg-Arg -Arg-Arg-Arg-Arg-Arg-Arg-Arg-Arg-Arg-Arg-Arg-Gly-Cys), SEQ ID NO:39 (Arg-Arg -Arg-Arg-Arg-Arg-Arg-Arg-Arg-Arg-Arg-Arg-Arg-Arg-Arg-Gly-Cys), SEQ ID NO:40 (Arg-Arg-Arg-Arg-Arg-Arg-Arg-Arg-Arg-Arg-Arg-Arg-Arg-Arg-Arg-Arg-Gly-Cys), SEQ ID NO:41 (Arg-Arg-Arg-Arg-Arg-Arg-Arg-Arg-Arg-Arg-Arg-Arg-Arg-Arg-Arg-Arg -Arg-Gly-Cys), SEQ ID NO:42 (Arg-Arg-Arg-Arg-Arg-Arg-Arg-Arg-Arg-Arg-Arg -Arg-Arg-Arg-Arg-Arg-Arg-Arg-Gly-Cys), SEQ ID NO:43 (Arg-Arg-Arg-Arg-Arg -Arg-Arg-Arg-Arg-Arg-Arg-Arg-Arg-Arg-Arg-Arg-Arg-Arg-Gly-Cys), SEQ ID NO:44 (Arg-Arg-Arg-Arg-Arg-Arg-Arg-Arg-Arg-Arg-Arg-Arg-Arg-Arg-Arg-Arg-Arg-Arg-Arg -Arg-Gly-Cys), and SEQ ID NO:45 (Kaposi's FGF signal sequence, full length Met -Ser-Gly-Asp-Gly-Thr-Ala-Ala-Val-Ala-Leu-Leu-Pro-Ala-Val-Leu-Leu-Ala-Leu-Leu -Ala-Pro).

In certain embodiments, the eukaryotic promoter is selected from the group consisting of: a cytomegalovirus promoter, a von Willebrand Factor (vWf) promoter, a Clara cell secretory protein (CCSP/UG) promoter, an osteoblast-specific osteocalcin promoter, an albumin promoter, a muscle creatine kinase (MCK) promoter, a mucin-1 (Muc-1) promoter, a carcino embryonic antigen (CEA) promoter, a prostate specific antigen (PSA) promoter, an epidermal growth factor receptor (ErbB2/HER-2) promoter, a Myc promoter, a L-plastin promoter, an alpha-fetoprotein (AFP) promoter, a hypoxia-responsive element (HRE) promoter, an early growth response (egr-1) promoter, a multidrug resistance (mdr-1) promoter, a heat shock protein 70 (hsp70) promoter, a tetracycline induced promoter, a simian virus 40

(SV40) promoter, an alcohol dehydrogenase (ADH1) promoter, a GAL4 promoter, and a LexA promoter.

Examples of RNAP promoters include, without limitation, the following:
TAATACGACTCACTATAGGGAGA (SEQ ID NO: 22) for T7 RNAP,
ATTTAGGTGACACTATAGAAGAA (SEQ ID NO: 23) for SP6 RNAP,
AATTAACCCTCACTAAAGGGAGA (SEQ ID NO: 24) for T3 RNAP, and
AATTAGGGCACACTATAGGGAGA (SEQ ID NO: 25) for K11 RNAP.

Products of interest include, for example, a restriction endonuclease, a single-chain insulin, a cytokine, a non-therapeutic protein, a therapeutic protein. In certain embodiments, the product of interest is a therapeutic product. The therapeutic products can be chosen from a wide variety of compounds including, without limitation, a protein, a nucleic acid, an antisense nucleic acid, ribozymes, tRNA, snRNA, and an antigen. In certain embodiments, the therapeutic product encodes proteins that are exemplified by proteins chosen from the following group: a herpes simplex virus thymidine kinase (HSV-TK), a cytosine deaminase, a xanthine-guaninephosphoribosyl transferase, a p53, purine nucleoside phosphorylase, and a cytochrome P450 2B1. In other embodiments, the therapeutic product encodes a protein selected from the group consisting of: p53, a calmodulin-dependent seine threonine (DAP kinase), p16, a protein from an alternative reading frame of p16 (ARF), an adenomatous polyposis coli gene product (APC), neurofibromin, phosphatase and tensin homologue deleted from chromosome 10 (PTEN), a Wilms' tumor gene product (WT1), a neurofibromatosis type 1 gene product (NF1), an Apoptin, and a von Hippel-Lindau tumor suppressor gene product (VHL). In still other embodiments, the therapeutic product encodes a protein selected from the group consisting of: angiostatin, endostatin, and vascular endothelial growth factor (VEGF)-R2. The therapeutic products can also be a cytokine, including without limitation: IL-2, IL-3, IL-4, IL-6, IL-7, IL-10, IL-12, IL-15, IFN-α, IFN-β, IFN-γ, TNF-α, GM-CSF, G-CSF, and Fms-like tyrosine kinase 3 (Flt3)-Ligand. Other therapeutic products include, without limitation, an antibody (e.g., a single chain antibody, a peptide hormone, EPO, a single-chain insulin, etc.

In yet another aspect, the present invention provides for nucleic acid compositions comprising: a first nucleic acid molecule comprising a secretable RNA polymerase expression cassette, comprising a eukaryotic promoter operably linked to a nucleic acid encoding a secretable RNA polymerase, the sRNAP comprising a RNA polymerase and a secretion domain; and a second nucleic acid molecule comprising an expression cassette comprised of a RNA polymerase promoter operably linked to a nucleic acid encoding a product of interest. In certain embodiments, the secretable RNA polymerase expression cassette further comprises a RNA polymerase promoter operably linked to the nucleic acid encoding the secretable RNA polymerase.

Another aspect of the invention provides for lipid-nucleic acid compositions comprising a nucleic acid-lipid particle comprising a lipid portion and a nucleic acid portion, the nucleic acid portion comprising a secretable RNA polymerase expression cassette. The sRNAP expression cassette comprises a eukaryotic promoter operably linked to a nucleic acid encoding a secretable RNA polymerase comprising a RNA polymerase and a secretion domain; and a RNA polymerase operably linked to a nucleic acid encoding a product of interest. In certain embodiments, the nucleic acid-lipid particle is a serum-stable nucleic acid-lipid particle comprising a nucleic acid fully encapsulated within the lipid portion. The lipid portion can be composed of a variety of different lipids and various proportions of lipids. In certain embodiments, the lipid portion contains a protonatable lipid having a pKa in the range of about 4 to about 11. In particularly preferred embodiments, the lipid portion contains a cationic lipid. Examples of cationic lipids include, without limitation, DODAC, DODAP, DODMA, DOTAP, DOTMA, DC-Chol, DMRIE, and DSDAC. In another preferred embodiment, the lipid portion contains a bilayer stabilizing component, such as a PEG-lipid derivative or an ATTA-lipid derivative In yet another aspect, the present invention provides methods of expressing a nucleic acid encoding a product of interest in a cell. These methods involve introducing into a cell an expression cassette comprised of a RNA polymerase promoter operably linked to a nucleic acid encoding a product of interest; and contacting the cell with a secretable RNA polymerase comprising a RNA polymerase and a secretion domain. In certain embodiments, the cell contains a secretable RNA polymerase expression cassette comprised of a eukaryotic promoter operably linked to a nucleic acid encoding a secretable RNA polymerase, wherein the secretable RNA polymerase contains a RNA polymerase and a secretion domain. In certain embodiments, the secretable RNA polymerase is expressed from a cell comprising a secretable RNA polymerase expression cassette comprised of a eukaryotic promoter operably linked to a nucleic acid encoding a secretable RNA polymerase, wherein the secretable RNA polymerase contains a RNA polymerase and a secretion domain. In other embodiments, the secretable RNA polymerase being contacted with the cell is a purified secretable RNA polymerase. Preferably the expression cassette encoding the therapeutic product is present on the same nucleic acid molecule as the secretable RNA polymerase expression cassette.

In still yet another aspect, the present provides for methods of treating a disease in a subject, involving administering a therapeutically effective amount of an expression cassette comprised of a RNA polymerase promoter operably linked to a nucleic acid encoding a therapeutic product, and administering a therapeutically effective amount of a secretable RNA polymerase, wherein the secretable RNA polymerase comprises a RNA polymerase and a secretion domain. In certain embodiments, the secretable RNA polymerase is expressed from a secretable RNA polymerase expression cassette comprising a eukaryotic promoter operably linked to a nucleic acid encoding a secretable RNA polymerase, wherein the secretable RNA polymerase contains a RNA polymerase and a secretion domain. In certain embodiments, the secretable RNA polymerase expression cassette further contains a RNA polymerase promoter operably linked to the nucleic acid encoding a secretable RNA polymerase. Preferably the expression cassette encoding the therapeutic product is present on the same nucleic acid molecule as the secretable RNA polymerase expression cassette. In other embodiments, the expression cassette encoding the therapeutic product is present on a first nucleic acid molecule and the secretable RNA polymerase expression cassette is present on a second nucleic acid molecule.

The therapeutic products used in these methods can essentially be any therapeutic product that is efficacious in the treatment or amelioration of a disease or condition. Examples of diseases and conditions that can be treated using the methods of the present invention include, without limitation, the following: cancer, autoimmune disease, hemophilia, arthritis, cardiovascular disease, cystic fibrosis, sickle cell anemia, infectious disease, viral disease, AIDS, herpes, bacterial disease, pneumonia, tuberculosis and an inflammatory disease. Examples of therapeutic products include, without limitation, a protein, a nucleic acid, an antisense nucleic acid, and an antigen. In certain embodiments, enzymes and proteins that are cytotoxic by themselves or in conjunction with a prodrug are useful in treating cancer and other conditions. These enzymes and proteins include, without limitation, a herpes simplex virus thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, and a cytochrome P450 2B1. In other embodiments, cytokines and immunomodulators are useful as therapeutic products when used in methods of the present invention. Examples of useful cytokines include, without limitation, the following: IL-2, IL-3, IL-4, IL-6, IL-7, IL-10, IL-12, IL-15, IFN-α, IFN-β, IFN-γ, TNF-α, GM-CSF, G-CSF, and Flt3-Ligand.

These and other aspects of the present invention will become apparent upon reference to the following detailed description.

Figure 1:
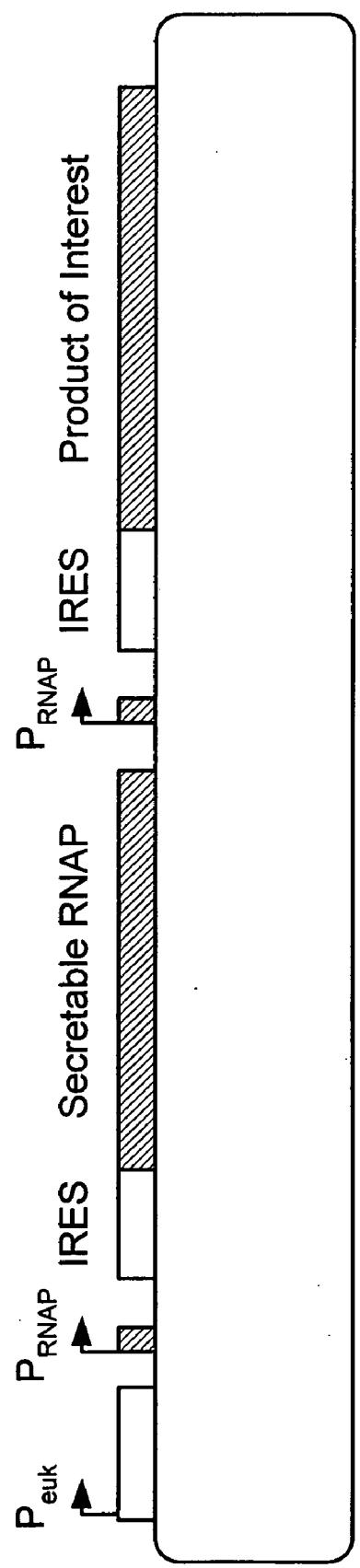
FIG. 1 depicts the secretable RNA polymerase expression cassette of the present invention.

Rusnati, et al. "Interaction HIV-1 Tat Protein with Heparin," The Journal of Biological Chemistry, 1997, vol. 272, No. 17, pp. 11313-11320.

DETAILED DESCRIPTION OF THE INVENTION

I. Introduction

The present invention provides nucleic acids and methods of expressing a product of interest in a cell. In some embodiments, the nucleic acids comprise expression cassettes comprising a eukaryotic promoter and a RNA polymerase promoter operably linked to a nucleic acid encoding a secretable RNA polymerase comprising a RNA polymerase and a secretion domain; and a RNA polymerase promoter operably linked to a nucleic acid encoding a product of interest. To express a product of interest, the expression cassette is introduced into a suitable cell. Preferably the expression cassette encoding the therapeutic product is present on the same nucleic acid molecule as the secretable RNA polymerase expression cassette.

In other embodiments, expression cassettes encoding a product of interest are present in the cytoplasm of a cell and a secretable RNA Polymerase (RNAP) is introduced into that cell. The secretable RNAP then transcribes the expression cassette encoding the product of interest. In certain embodiments, the present invention involves generating sRNAPs that are then contacted with and enter a cell that contains an expression cassette with a RNAP promoter operably linked to a nucleic acid encoding a product of interest. Preferably the expression cassette encoding the therapeutic product is present on the same nucleic acid molecule as the secretable RNA polymerase expression cassette.

In both of the embodiments described above, the product of interest can be a product that is purified and used as a pharmaceutical (e.g., single-chain insulin, EPO, a cytokine, etc.). In other embodiments, the products are therapeutic products that are expressed in a subject suffering from a disease. The production of a therapeutically effective amount of the therapeutic product in the subject is useful for the treatment of the disease that is afflicting the subject. These methods and components will be described in more detail below.

II. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "RNA polymerase" (RNAP) refers to a protein that is able to catalyze the polymerization of RNA from DNA.

A "secretable RNA polymerase" is a molecule that contains a RNA polymerase linked to a secretion domain. A "secretable RNA Polymerase" (sRNAP) is able to enter the cytoplasm of a cell when contacted with the outside of the cell or the cell.

A "secretion domain" is a polypeptide sequence that when linked to another polypeptide creates a fusion protein that is able to enter a cell when contacted with that cell.

Examples of secretion domains include, without limitation, SEQ ID NOS: 1, 2, 3, 4, 5, 6, 7, 8, 9, 10, 11, 12, 13, 14, 15, 16, 17, 18, 19, 20, and 21.

A "non-host RNA polymerase" is a RNAP that is not naturally encoded by the nuclear genome of a eukaryotic organism.

A "phagemid RNA polymerase" is a RNAP from a bacteriophage (e.g., T3, T7, SP6, and K11 bacteriophages).

A "SP6 RNA Polymerase" is a RNAP encoded by a nucleic acid that is about 90% or more identical to GenBank Accession No. Y00105.

A "T7 RNA Polymerase" is a RNAP encoded by a nucleic acid that is about 90% or more identical to GenBank Accession No. M38308.

A "K11 RNA Polymerase" is a RNAP encoded by a nucleic acid that is about 90% or more identical to GenBank Accession No. X53238.

A "T3 RNA Polymerase" is a RNAP encoded by a nucleic acid that is about 90% or more identical to GenBank Accession No. X02981.

An "expression cassette" is a polynucleotide sequence that contains a nucleic acid coding sequence for a protein, polypeptide, antisense nucleic acid, sense nucleic acid, etc., and the necessary control elements (e.g., promoter sequence(s), transcription start site, translation start site, etc) for expression of the nucleic acid coding sequence. One or more expression cassettes can be on a single nucleic acid molecule, e.g,. a plasmid, a vector, etc.

A "secretable RNA polymerase expression cassette" is an expression cassette that encodes a secretable RNA polymerase (sRNAP).

The term "eukaryotic promoter" refers to a nucleic acid sequence that when operably linked to a nucleic acid, permits transcription of that nucleic acid in the nucleus of a eukaryotic cell.

A promoter is "operably linked" to a nucleic acid when the relationship between the promoter and the nucleic acid is such that expression of the nucleic acid can take place. The promoter does not have to be contiguous with the nucleic acid, i.e., there can be intervening nucleic acid sequences between the nucleic acid and the promoter.

A "RNA polymerase promoter" is a nucleic acid comprising a sequence of nucleotides to which a RNA polymerase can bind to and activate transcription.

A "therapeutic product" is a compound, (e.g., a protein, a nucleic acid, a hormone, an antisense nucleic acid, an antigen, etc.) that can be used to treat or ameliorate a disease or condition.

The term "serum-stable" in relation to a nucleic acid-lipid particle means that the nucleic acid is fully encapsulated by the lipid portion of the nucleic acid-lipid particle such that less than 5% of the nucleic acid is degraded after exposure of the nucleic acid-lipid particle to 1 U DNAse I for 30 minutes in digestion buffer at 37° C.

The term "cationic lipid" refers to any of a number of lipid species that carry a net positive charge at a selected pH, such as physiological pH. Such lipids include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate ("DOSPA") and("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). The following lipids are cationic and have a positive charge at below physiological pH: DODAP, DODMA, DMDMA and the like.

A "purified secretable RNA polymerase" is a secretable RNAP that is at least 50% pure.

"Therapeutically effective amount," as used herein, refers to an amount of a compound (e.g., drug, nucleic acid, etc.) that is sufficient or necessary to give rise to a desired therapeutic effect. The therapeutic effect can be obtained directly or indirectly. For instance, the therapeutic agent can lead to activation of other therapeutic agents or can act in combination with additional therapeutic agents. For neoplasia, a therapeutic effect can be, for example, a reduction in growth, inhibition or reduction in size of the neoplasia or inhibition or reduction of metastasis and other malignant attributes, or other beneficial effects, such as subjective or objective observations of physicians and patients.

III. Secretable RNAPs

The secretable RNAPs of the present invention comprise a secretion domain and a RNAP domain. Typically, RNAPs are not secretable in that they are not secreted from cells and are not able to enter a cell. However, there are protein sequences known in the art, secretion domains, that when attached to a cargo peptide, that is not secretable, generates a secretion domain fused to a cargo peptide that is competent to enter a cell. Thus, the attachment of a secretion domain to the N- or C-terminus of a RNAP generates a secretable RNAP (sRNAP). The secretion domain may be expressed as a fusion protein comprising the secretion domain and the RNAP domain or can be the result of chemically linking the secretion domain to the RNAP domain. The connection between the secretion domain and the fusion protein can be direct or there can be a linker between them. The presence of a linker can be advantageous for the function of the molecule.

A. RNA Polymerases

It is preferred that the RNAP is a non-host RNA Polymerase that is active in the cytoplasm of a eukaryotic cell. Examples of RNAPs that are useful in the present invention include, without limitation, a phagemid RNA polymerase, a prokaryotic RNA polymerase, an archaebacterial RNA polymerase, a plant RNA polymerase, a fungal RNA polymerase, a eukaryotic RNA polymerase, a viral RNA polymerase, a mitochondrial RNA polymerase, and a chloroplast RNA polymerase. In particularly preferred embodiments, the phagemid RNAP is from a bacteriophage and encodes a single chain RNAP that is active as a monomer or higher order homomer (e.g., dimer). Particularly preferred phagemid RNAPs include, a SP6 RNAP (e.g., GenBank Accession No. Y00105), a T7 RNAP (e.g., GenBank Accession No. M38308), a T3 RNAP (e.g., GenBank Accession No X02981), and a K11 RNAP (e.g., GenBank Accession No. X53238; (Dietz et al. (1990) *Mol. Gen. Genet.* 221: 283-286). These phagemid RNAPs have been cloned and expressed in bacteria and several are commercially available (e.g,. SP6 RNAP, T7 RNAP, T3 RNAP). For example, the T7 RNAP (Davanloo et al. (1984) *Proc. Natl. Acad. Sci., U.S.A.* 81: 2035-2039) and the K11 RNAP (Han et al. (1999) *Protein Expr. Purif.* 16: 103-108) have been expressed as soluble proteins in *E. coli.*

The sRNAPs of the present invention should retain the enzymatic activity of the native RNAP, i.e., the ability to carry out template dependent synthesis of RNA. For example, the functionality of a sRNAP can be assessed using in vitro transcription and translation assays. One such assay utilizes a commercially available rabbit reticulocyte lysate, a cell-free reagent which contains all of the ribosomes and components needed for transcription and translation. The cell-free lysate is incubated with the sRNAP and a plasmid encoding a luciferase reporter plasmid. The luciferase reporter plasmid has a RNAP promoter specific for the sRNAP operably linked to a luciferase gene. If the sRNAP is able to transcribe the luciferase gene, then luciferase will be present in the sample and can be assayed using a luminometer.

In addition, the sRNAPs should be able to enter into a cell. One method of assaying whether a sRNAP can enter a cell is to tranfect two separate populations of cells. The first population is transfected with a nucleic acid comprising a sRNAP expression cassette. The second population of cells is tranfected with a nucleic acid comprising a luciferase reporter plasmid that has a RNAP promoter specific for the sRNAP operably linked to a luciferase gene or a product of interest. After the transfection, the two populations are mixed and luciferase activity is assayed. The presence of luciferase will confirm that the sRNAP protein was transported inter-cellularly in order to activate luciferase expression in neighboring cells. Similarly, an assay for the product of interest can be carried out to test whether the sRNAP is functional. Alternatively, purified sRNAP or cell culture media from the first population of cells just described is incubated with the second population of cells comprising the RNAP promoter driven luciferase expression cassette. The presence of luciferase activity is an indication that the sRNAP can enter into a cell.

B. Secretion Domain

The secretion domains when fused to the RNAP should generate a sRNAP. That is the sRNAP will have the ability to enter a cell from the outside and pass into the cytoplasm, such that the sRNAP can carry out transcription of an expression cassette containing a RNAP promoter. In certain embodiments of the present invention, the secretion domain targets the sRNAP to the cytoplasm of the cell. For example, the secretion domains can be chosen from the following secretion domains: SEQ ID NOS: 1, 2, 3, 4, 5, 6, 7, 8, 9, 10, 11, 12, 13, 14, 15, 16, 17, 18, 19, 20, and 21.

Several classes of secretion domains are known in the art. Examples of classes of secretion domains include signal peptides and protein transduction domains, both of which are described below.

1. Signal Peptides

Signal peptide sequences are hydrophobic peptides that mediate translocation of many secretory proteins across membranes (see, von Heijne (1990) *J. Membrane Biol.* 115: 195-201). Signal peptide sequences can be chosen from databases, such as the SIGPEP database (von Heijne (1987) *Protein Sequence Data Analysis* 1: 41-42; von Heijne and Abrahmsen (1989) *FEBS Letters* 224: 439-446). Examples of signal peptides include the signal peptide sequences for IL-2 (e.g., SEQ ID NOS: 19 and 20).

A particularly preferred class of signal peptides that can be used as secretion domains are importation competent signal peptides which permit cargo peptides to be imported into a cell as an importation competent signal peptide-cargo fusion protein (see, e.g., U.S. Pat. No. 5,807,746 and U.S. Pat. No. 6,043,339). An importation competent signal peptide is hydrophobic in nature and comprises about 55-60% hydrophobic residues such that it is capable of being secreted from a cell and can penetrate a cell membrane when contacted with the outside of the cell. In certain embodiments, the importation competent signal peptide is a sequence of amino acids generally of a length from about 10 to about 50 or more amino acids. A preferred importation competent signal peptide is SEQ ID NO: 18, the signal peptide of K-FGF (Kaposi Fibroblast growth factor).

2. Protein Transduction Domains

Protein transduction domains (PTDs) have been described in the art and are small regions of proteins that have the ability to traverse biological membranes in a receptor and transporter-independent manner (reviewed in Schwarze and Dowdy (2000) *Trends Pharmacol. Sci.* 21(2):45-48). Cargo proteins when linked to protein transduction domains can also traverse biological membranes (see, Schwarze and Dowdy (2000) *Trends Pharmacol. Sci.* 21(2):45-48). Examples of PTDs include, without limitation, VP22, Tat, and the third helix of the Drosophila homeodomain transcription factor ANTP. The minimal regions for these PTDs have been described as being residues 47-57 of Tat, residues 267-300 of VP22, and residues 43-58 of ANTP.

a) VP22 Peptides and VP22 Analog Peptides

A Herpesvirus structural protein, VP22, when fused to cargo proteins can be rapidly taken up by eukaryotic cells (see, e.g., U.S. Pat. No. 6,017,735; U.S. Pat. No. 6,184,038; Elliott and O'Hare (1997) *Cell* 88(2):223-233; Elliott and O'Hare (1999) *Gene Ther.* 6(1):149-151; and Aints et al. (1999) *J. Gene Med.* 1:275-279). This uptake process appears to occur via a non-classical Golgi-independent mechanism. VP22 can be fused to the N- or C-terminus of a heterologous protein to generate a secretable protein. In addition, VP22-fusion protein import and export does not appear to be limited to particular cell type (Elliott and O'Hare (1997); Wybranietz et al. (1999) *J. Gene Med.* 1(4):265-274). For example, VP22-GFP proteins were expressed by and spread intercellularly by cell types such as HepG2 (human hepatoma), Hep3B (human hepatoma), HuH7 (human hepatoma), HeLa (human cervix adenocarcinoma), MCF-7 (human mammary carcinoma), HEK-293 (human embryo kidney), CV-1 (monkey kidney), COS-1 (monkey kidney), NIH-3T3 (mouse fibroblast), and M-12 (canine kidney) (Wybranietz et al. (1999) *J. Gene Med.* 1(4):265-274)). A VP22-p53 and a p53-VP22 fusion protein were both able to efficiently induce apoptosis in p53 negative osteosarcoma cells, indicating that these proteins are useful for inducing cytotoxicity in tumorigenic cells (Phelan et al. (1998) *Nat. Biotechnol.* 16(5):440-443). Similarly, VP22-tk and tk-VP22 fusion proteins were effective at killing cells in vitro and a neuroblastoma tumor in vivo when ganciclovir was co-administered (Dilber et al. (1999) *Gene Ther.* 6(1):12-21).

b) Antennapedia Third Helix Peptides

Peptides comprising the third Helix of the ANTP transcription factor (e.g., amino acids 43-58) when fused to a cargo oligopeptide or cargo oligonucleotides can be translocated across a plasma membrane (Derossi et al. (1998) *Trends Cell Biol.* 8:84-87). For example, U.S. Pat. No. 5,888,762 describes macromolecules that are able to enter a living cell by virtue of a peptide fragment corresponding to the third helix of the Antennapedia homoeodomain (residues 43-58). Examples of useful Antennapedia third helix sequences are SEQ ID NOS: 10, 11, 12, 13, 14, 15, 16, and 17 (Prochiantz (2000) *Curr. Opin. Cell Biol.* 12:400-406; Derossi et al. (1998)).

c) TAT Peptides and Analogs Thereof

In certain embodiments of the present invention, the protein transduction domain is comprised of a tat sequence or a variant thereof. Tat sequences, and variant thereof, have been heterologously fused to cargo peptides. These tat-cargo peptides are able to enter cells by contacting them with the outside of the cell. Tat sequences that are useful as secretion domains include, without limitation, SEQ ID NOS: 1, 2, 3, 4, 5, 6, 7, and 8 (see, e.g., WO 99/29721; WO 00/34308 and WO 00/62067). For example, when a 11-amino acid protein transduction domain from the HIV TAT protein was fused to β-galactosidase, a cell permeable Tat-βgal protein was created (see, Schwarze et al. (1999) *Science* 285(5433):1569-1572). When the Tat-β-gal protein was injected intraperitoneally into a mouse, staining for β-gal activity was found throughout the animal, including the heart, liver, kidney, lung, and muscle. Staining was also found in the brain, indicating that the tat-fusion proteins have the ability to cross the blood-brain barrier.

Methods for generating transducible Tat fusion proteins are known in the art (see e.g., Vocero-Akbani et al. (2000) *Methods Enzymol.* 322:508-521). The Tat fusion proteins can be tagged with an oligohistidine stretch on the N-terminus to facilitate purification. (Vocero-Akbani et al. (2000)). For example, a histidine tagged Tat domain (Arg-Lys-Lys-Arg-Arg-Gln-Arg-Arg-Arg; SEQ ID NO:46) when fused to the N-terminus of superoxide dismutatase (SOD) generates a Tat-SOD that can be expressed in *E. coli* and can enter HeLa cells when added to culture media (Kwon et al. (2000) *FEBS Lett.* 485(2-3): 163-167).

One of skill in the art can screen sRNAPs to see if a particular secretion domain confers the ability to enter cells using a variety of methods known to those of skill in the art. For example, the sRNAPs (or other secretion domain fusion proteins) can be labeled with a detectable label, such as a fluorescent label (e.g., fluorescein), and followed by FACS analysis (Vocero-Akbani et al. (2000)). In certain embodiments, purified denatured secretion domain fusion proteins are employed which can increase the efficiency of the biological response being measured or effected (see, e.g., Vocero-Akbani et al. (2000)).

3. Linker Regions

The secretion domains can be directly fused to the RNAP or a linker region (e.g., of amino acids) can be used to join the secretion domain to the RNAP. If the linker region is comprised of amino acids, then the linker sequence is preferably between 1 and 2-30 amino acids. The composition and arrangement of the amino acids in the linker region should permit the RNAP to retain its activity and allow the sRNAP to enter a cell.

C. Expression Cassettes Encoding a sRNAP

One way to generate the sRNAPs used in the present invention is to express them in a eukaryotic cell. In preferred embodiments, the sRNAPs are expressed from a cell containing a secretable RNA polymerase expression cassette. Typically, a sRNAP expression cassette contains a eukaryotic promoter operably linked to a nucleic acid encoding a secretable RNA polymerase. The promoter used to direct expression of a heterologous nucleic acid depends on the particular application. The promoter is preferably positioned about the same distance from the heterologous transcription start site for the sRNAP nucleic acid as it is from the transcription start site in its natural setting. As is known in the art, however, some variation in this distance can be accommodated without loss of promoter function. The promoter typically can also include elements that are responsive to transactivation, e.g., hypoxia responsive elements, Gal4 responsive elements, lac repressor responsive elements, and the like. Examples of eukaryotic promoters include a CMV promoter, a SV40 promoter, a ADH1 promoter, a GAL4 promoter, and a LexA promoter. The promoter can be constitutive or inducible, heterologous or homologous, as well as tissue-specific, or tumor-specific. Examples of suitable promoters are described in more detail below.

1. Tissue-Specific Promoters

For example, promoter sequences are known in the art that are active in specific cell types. Tissue-specific promoters have been described for endothelial cells (vWf promoter; see, e.g., Jahroudi and Lynch (1994) *Mol. Cell. Biol.*, 14(2): 999-1008), lung epithelium (CCSP promoter; see, e.g., Stripp et al. (1994) *Genomics* 20(1):27-35), liver (albumin promoter; (see, e.g., Gorski et al. (1986) *Cell* 47(5): 767-776), bone tissue (osteoblast-specific osteocalcin promoter; (see, e.g., Lian et al. (1989) *Connect. Tissue Res.* 21(1-4): 61-68), and muscle (MCK promoter; see, e.g., Jaynes et al. (1988) *Mol. Cell. Biol.* 8(1): 62-70).

2 Tumor-Specific Promoters

In certain embodiment, the eukaryotic promoter is a tumor-specific promoter. Tumor-specific promoters are known in the art: Muc-1 promoter: Spicer et al. (1991) *J. Biol. Chem.* 266(23): 15099-15109, CEA promoter (see, e.g., Schrewe et al. (1990) *Mol. Cell. Biol.* 10(6): 2738-2748), PSA-promoter (see, e.g., Riegman et al. (1991) *Mol. Endocrinol.* 5(12): 1921-1930), HER-2 promoter (see, e.g., Ishii et al. (1987) *Proc. Natl. Acad. Sci., U.S.A.* 84(13): 4374-4378), L-plastin promoter (see, e.g., Lin et al. (1993) *J. Biol. Chem.* 268(4): 2793-2801), AFP promoter (see, e.g., Widen and Papaconstantinou (1986) *Proc. Natl. Acad. Sci., U.S.A.* 83(21): 8196-8200). These tumor-specific promoters are active in particular kinds of tumors. For example, the L-plastin promoter is active in breast cancers, the AFP promoter is active in liver tumors and the HRE promoter is active in solid tumors.

3. Inducible Promoters

In addition, there are promoters whose activity can be induced upon an external stimulus, such as the addition of an exogenous compound or upon a change in environmental conditions such as a HRE promoter (see, e.g., Dachs et al. (1997) *Nat. Med.* 3(5): 515-520), a Egr-1 promoter (see, e.g., Hallahan et al. (1995) *Nat. Med.* 1(8): 786-791), a Mdr-1 promoter (see, e.g., Ueda et al. (1987) *J. Biol. Chem.* 262(36): 17432-17136), a Hsp70 promoter (see, e.g., Pelham and Bienz, (1982) *EMBO J.* 1(11): 1473-1477), and a tetracycline-induced promoter (see, e.g., Furth et al. (1994) *Proc. Natl. Acad. Sci., U.S.A.* 91(20): 9302-9306. These promoters are activated with various stimuli, including radiation for the egr-1 promoter, chemotherapy for the mdr-1 promoter, heat for the hsp-70 promoter and tetracycline for the tetracycline induced promoter.

In addition to the promoter, the expression cassette typically contains a transcription unit that contains all the additional elements required for the expression of the nucleic acid in host cells. A typical expression cassette thus can contain signals required for efficient polyadenylation of the transcript, ribosome binding sites (e.g., an IRES (Internal ribosomal entry site)), and a translation termination signal. Additional elements of the cassette may include enhancers and, if genomic DNA is used as the structural gene, introns with functional splice donor and acceptor sites.

Expression vectors containing the sRNAP expression cassette can be employed in the present invention. These vectors include SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells, such as those described above.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

4. RNAP Promoters

The expression cassettes encoding a sRNAP can also contain a RNAP promoter. In addition, the expression cassettes comprising a nucleic acid encoding a product of interest typically contain a RNAP promoter. The RNAP promoter should be recognized and competent to be transcribed by the sRNAP being employed. Preferably, the RNAP promoter is a non-host RNAP promoter. More preferably, the RNAP promoter is a phagemid promoter such as a T7 RNAP promoter, a SP6 RNAP promoter, a T3 RNAP promoter, and a K11 RNAP promoter. Examples of promoter nucleic acid sequences for phagemid RNAPs include, without limitation, TAATACGACTCACTATAGGGAGA (SEQ ID NO: 22) for T7 RNAP, ATTTAGGTGACACTATAGAAGAA (SEQ ID NO: 23) for SP6 RNAP, AATTAACCCTCACTAAAGGGAGA (SEQ ID NO: 24) for T3 RNAP, and AATTAGGGCACACTATAGGGAGA (SEQ ID NO: 25) for K11 RNAP (see e.g., Rong et al. (1999) Biotechniques 27: 690-694).

IV. Purified sRNAPs

Alternatively, the sRNAPs of the present invention can be purified from cell culture media of cells that express an sRNAP. The sRNAPs can be expressed in eukaryotic cells from a sRNAP coding sequence subcloned into a eukaryotic vector. Eukaryotic expression systems for mammalian cells, yeast, and insect cells are well known in the art and are also commercially available.

In addition, the sRNAPs of the present invention can be purified from prokaryotes. Bacterial expression systems for expressing the sRNAPs are available in, e.g., E. coli, Bacillus sp., and Salmonella (Palva et al., Gene 22:229-235 (1983)). Kits for such expression systems are commercially available. Phagemid RNAPs have been expressed in E. coli without secretion domains: T7 RNAP (Davanloo et al. (1984) Proc. Natl. Acad. Sci., U.S.A. 81: 2035-2039) and K11 RNAP (Han et al. (1999) Protein Expr. Purif. 16: 103-108).

If necessary, recombinant sRNAPs can be purified for use for use in expressing a product of interest and for preparing pharmaceutical compositions of sRNAPs. Recombinant sRNAPs can be purified from any suitable expression system, e.g., by expressing a sRNAP in E. coli and then purifying the recombinant protein via affinity purification, e.g., by using antibodies that recognize a specific epitope on the protein or on part of the fusion protein, or by using glutathione affinity gel, which binds to GST. In some embodiments, the recombinant protein is a fusion protein, e.g., a histidine tagged sRNAP, a GST tagged sRNAP, etc.

The sRNAP may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra). Preferably, the sRNAP is purified to at least 50% purity, even more preferably to at least 80% purity, still more preferably to at least 90% purity, and yet still more preferably to at least 95% purity.

A number of procedures can be employed when recombinant sRNAPs are being purified. For example, proteins having established molecular adhesion properties can be reversibly fused to a sRNAP. With the appropriate ligand, sRNAP can be selectively adsorbed to a purification column and then freed from the column in a relatively pure form. The fused protein is then removed by enzymatic activity. Finally, a sRNAP can be purified using immunoaffinity columns.

1. Purification of sRNAP from Recombinant Bacteria

Recombinant sRNAPs are expressed by transformed bacteria in large amounts, typically after promoter induction, but expression can be constitutive. Promoter induction with IPTG is one example of an inducible promoter system. Bacteria are grown according to standard procedures in the art. Fresh or frozen bacteria cells are used for isolation of protein.

sRNAPs expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. sRNAPs that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example, SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The sRNAP of choice is separated from other bacterial proteins by standard separation techniques, e.g., with Ni-NTA agarose resin.

2. Standard Protein Separation Techniques for Purifying sRNAPs a) Solubility Fractionation

Often as an initial step, particularly if the protein mixture is complex, an initial salt fractionation can separate many of the unwanted host cell proteins (or proteins derived from the cell culture media) from the recombinant sRNAP of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

b) Size Differential Filtration

The molecular weight of the protein, e.g., a sRNAP, can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant sRNAP will pass through the membrane into the filtrate. The filtrate can then be chromatographed as described below.

c) Column Chromatography

The sRNAP of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Expression Cassettes Encoding a Product of Interest

The expression cassettes encoding a product of interest can be on the same molecule or on a different molecule than the expression cassette encoding a sRNAP. Thus, in certain embodiments, the nucleic acid containing a sRNAP expression cassette also contains an expression cassette containing a RNA polymerase promoter operably linked to a nucleic acid encoding a product of interest. In other embodiments, the expression cassette encoding a product of interest is on a second nucleic acid molecule comprising an expression cassette containing a RNA polymerase promoter operably linked to a nucleic acid encoding a product of interest. Preferably the expression cassette encoding the therapeutic product is present on the same nucleic acid molecule as the secretable RNA polymerase expression cassette. These expression cassettes are constructed using standard molecular biology techniques similar to those used to construct the expression cassettes encoding the sRNAP.

A. Products of Interest

The RNAP promoter can be transcribed by a sRNAP that enters the cell, leading to the expression of the product of interest. The product of interest can be useful for commercial purposes, including for therapeutic purposes as a pharmaceutical or for diagnostic purposes. Some products of interest are therapeutic products. Some therapeutic products of interest (e.g., single-chain insulin, EPO) can be purified, formulated as a pharmaceutical composition and used for the treatment of a disease (e.g., diabetes, anemia, etc). In certain embodiments, the therapeutic product itself can also be a fusion protein between a secretable domain and a product of interest. Examples of therapeutic products include a protein, a nucleic acid, an antisense nucleic acid, ribozymes, tRNA, snRNA, an antigen, Factor VIII, and Apoptin (Zhuang et al. (1995) *Cancer Res.* 55(3): 486-489). Suitable classes of gene products include, but are not limited to, cytotoxic/suicide genes, immunomodulators, cell receptor ligands, tumor suppressors, and anti-angiogenic genes. The particular gene selected will depend on the intended purpose or treatment. Examples of such genes of interest are described below and throughout the specification.

1. Tumor Suppressors

Tumor suppressor genes are genes that are able to inhibit the growth of a cell, particularly tumor cells. Thus, delivery of these genes to tumor cells is useful in the treatment of cancers. Tumor suppressor genes include, but are not limited to, p53 (Lamb et al., *Mol. Cell. Biol.* 6:1379-1385 (1986), Ewen et al., *Science* 255:85-87 (1992), Ewen et al. (1991) *Cell*66:1155 -1164, and Hu et al., *EMBO J.* 9:1147-1155 (1990)), RB1 (Toguchida et al. (1993) *Genomics* 17:535-543), WT1 (Hastie, N. D., *Curr. Opin. Genet. Dev.* 3:408-413 (1993)), NF1 (Trofatter et al., *Cell* 72:791-800 (1993), Cawthon et al., *Cell* 62:193-201 (1990)), VHL (Latif et al., *Science* 260:1317-1320 (1993)), APC (Groden et al., *Cell* 66:589-600 (1991)), DAP kinase (see e.g., Deiss et al. (1995) *Genes Dev.* 9:15-30), p16 (see e.g., Marx (1994) *Science* 264(5167): 1846), ARF (see e.g., Quelle et al. (1995) *Cell* 83(6): 993-1000), Neurofibromin (see e.g., Huynh et al. (1992) *Neurosci. Lett.* 143(1-2): 233-236), Apoptin (Zhuang et al. (1995) *Cancer Res.* 55(3): 486-489), and PTEN (see e.g., Li et al. (1997) *Science* 275(5308): 1943-1947).

2. Immunomodulator Genes

Immunomodulator genes are genes that modulate one or more immune responses. Examples of immunomodulator genes include cytokines such as growth factors (e.g., TGF-α., TGF-β, EGF, FGF, IGF, NGF, PDGF, CGF, GM-CSF, G-CSF, SCF, etc.), interleukins (e.g., IL-2, IL-3, IL-4, IL-6, IL-7, IL-10, IL-12, IL-15, IL-20, etc.), interferons (e.g., IFN-α, IFN-β, IFN-γ, etc.), TNF (e.g., TNF-α), and Flt3-Ligand.

3. Cell Receptor Ligands

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g,. inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, single-chain insulin (Lee et al. (2000) *Nature* 408: 483-488), glucagon, G-protein coupled receptor ligands, etc.). These cell surface ligands can be useful in the treatment of patients suffering from a disease. For example, a single-chain insulin when expressed under the control of the glucose-responsive hepatocyte-specific L-type pyruvate kinase (LPK) promoter was able to cause the remission of diabetes in streptocozin-induced diabetic rats and autoimmune diabetic mice without side effects (Lee et al. (2000) *Nature* 408:483-488). This single-chain insulin was created by replacing the 35 amino acid resides of the C-peptide of insulin with a short turn-forming heptapeptide (Gly-Gly-Gly-Pro-Gly-Lys-Arg; SEQ ID NO:47).

4. Anti-Angiogenic Genes

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see e.g., U.S. Pat. No. 6,174,861), angiostatin (see, e.g., U.S. Pat. No. 5,639,725), and VEGF-R2 (see e.g., Decaussin et al (1999) *J. Pathol.* 188(4): 369-737).

5. Cytotoxic/Suicide Genes

Cytotoxic/suicide genes are those genes that are capable of directly or indirectly killing cells, causing apoptosis, or arresting cells in the cell cycle. Such genes include, but are not limited to, genes for immunotoxins, a herpes simplex virus thymidine kinase (HSV-TK), a cytosine deaminase, a xanthine-guaninephosphoribosyl transferase, a p53, a purine nucleoside phosphorylase, a carboxylesterase, a deoxycytidine kinase, a nitroreductase, a thymidine phosphorylase, and a cytochrome P450 2B1.

In a gene therapy technique known as gene-delivered enzyme prodrug therapy ("GDEPT") or, alternatively, the "suicide gene/prodrug" system, agents such as acyclovir and ganciclovir (for thymidine kinase), cyclophosphoamide (for cytochrome P450 2B1), 5-fluorocytosine (for cytosine deaminase), are typically administered systemically in conjunction (e.g., simulatenously or nonsimulatenously, for example, sequentially) with a expression cassette encoding a suicide gene compositions of the present invention to achieve the desired cytotoxic or cytostatic effect (see, e.g., Moolten, F. L., *Cancer Res.*, 46:5276-5281 (1986)). For a review of the GDEPT system, see, Moolten, F. L., *The Internet Book of Gene Therapy, Cancer Therapeutics*, Chapter 11 (Sobol, R. E., Scanlon, N J (Eds) Appelton & Lange (1995)). In this method, a heterologous gene is delivered to a cell in an expression cassette containing a RNAP promoter, the heterologous gene encoding an enzyme that promotes the metabolism of a first compound to which the cell is less sensitive (i.e., the "prodrug") into a second compound to which is cell is more sensitive. The prodrug is delivered to the cell either with the gene or after delivery of the gene. The enzyme will process the prodrug into the second compound and respond accordingly. A suitable system proposed by Moolten is the herpes simplex virus-thymidine kinase (HSV-TK) gene and the prodrug ganciclovir. This method has recently been employed using cationic lipid-nucleic aggregates for local delivery (i.e., direct intra-tumoral injection), or regional delivery (i.e., intra-peritoneal) of the TK gene to mouse tumors by Zerrouqui, et al., *Can. Gen. Therapy*, 3(6):385-392 (1996); Sugaya, et al., *Hum. Gen. Ther.*, 7:223-230 (1996) and Aoki, et al., *Hum. Gen. Ther.*, 8:1105-1113 (1997). Human clinical trials using a GDEPT system employing viral vectors have been proposed (see, *Hum. Gene Ther.*, 8:597-613 (1997), and *Hum. Gene Ther.*, 7:255-267 (1996)) and are underway.

For use with the instant invention, the most preferred therapeutic products are those which are useful in gene-delivered enzyme prodrug therapy ("GDEPT"). Any suicide gene/prodrug combination can be used in accordance with the present invention. Several suicide gene/prodrug combinations suitable for use in the present invention are cited in Sikora, K. in OECD Documents, Gene Delivery Systems at pp.59-71 (1996), incorporated herein by reference, include, but are not limited to, the following:

| Suicide Gene Product | Less Active ProDrug | Activated Drug |
|---|---|---|
| Herpes simplex virus type I thymidine kinase (HSV-TK) | ganciclovir(GCV), acyclovir, bromovinyl-deoxyuridine, or other substrates | phosphorylated dGTP analogs |
| Cytosine Deaminase (CD) | 5-fluorocytosine | 5-fluorouracil |
| Xanthine-guanine-phosphoribosyl transferase (XGPRT) | 6-thioxanthine (6TX) | 6-thioguano-sinemonophosphate |
| Purine nucleoside phosphorylase | MeP-dr | 6-methylpurine |
| Cytochrome P450 2B1 | cyclophosphamide | [cytotoxic metabolites] |
| Linamarase | amygdalin | cyanide |
| Nitroreductase | CB 1954 | nitrobenzamidine |
| Beta-lactamase | PD | PD mustard |
| Beta-glucuronidase | adria-glu | adriamycin |
| Carboxypeptidase | MTX-alanine | MTX |
| Glucose oxidase | glucose | peroxide |
| Penicillin amidase | adria-PA | adriamycin |
| Superoxide dismutase | XRT | DNA damaging agent |
| Ribonuclease | RNA | cleavage products |

Any prodrug can be used if it is metabolized by the heterologous gene product into a compound to which the cell is more sensitive. Preferably, cells are at least 10-fold more sensitive to the metabolite than the prodrug.

Modifications of the GDEPT system that may be useful with the invention include, for example, the use of a modified TK enzyme construct, wherein the TK gene has been mutated to cause more rapid conversion of prodrug to drug (see, for example, Black, et al., *Proc. Natl. Acad. Sci, U.S.A.*, 93: 3525-3529 (1996)). Alternatively, the TK gene can be delivered in a bicistronic construct with another gene that enhances its effect. For example, to enhance the "bystander effect" also known as the "neighbor effect" (wherein cells in the vicinity of the transfected cell are also killed), the TK gene can be delivered with a gene for a gap junction protein, such as connexin 43. The connexin protein allows diffusion of toxic products of the TK enzyme from one cell into another. The TK/Connexin 43 construct has a CMV promoter operably linked to a TK gene by an internal ribosome entry sequence and a Connexin 43-encoding nucleic acid.

VI. Methods for Introducing Expression Cassettes into Cells

Methods are well known in the art for introducing nucleic acids into cells. (see, e.g., CURRENT PROTOCOLS IN MOLECULAR BIOLOGY (Ausubel, et al. (eds.) 1995). These methods can be used to introduce into cells a nucleic acid containing an expression cassette comprised of a RNA polymerase promoter operably linked to a nucleic acid encoding a product of interest, as well as an expression cassette encoding a sRNAP. The expression cassettes can be introduced into the same cell on the same molecule, into the same cell on different molecules, into different cells on two different molecules, etc. Methods such as biollistics, transfection, electroporation, viral delivery systems, etc. can be employed in the present invention. In addition, the nucleic acids can be formulated using a variety of compounds known in the art for packaging nucleic acids for introduction into cells, such as polylysine, polyethylenimine (PEI), DEAE-dextran, and lipids.

In preferred embodiments, the nucleic acids of the present invention are delivered into cells as a lipid-nucleic acid composition containing a nucleic acid-lipid particle comprising a lipid portion and a nucleic acid portion. In particularly preferred embodiments the lipid-nucleic acid composition is a stabilized-stable lipid particle, wherein the nucleic acid is fully encapsulated within said lipid portion (see, e.g., Wheeler et al. (1999) *Gene Therapy* 6: 271-281). Preferred lipids include those protonatable lipids having a pKa in a range of about 4 to about 11. Cationic lipids are also useful in formulating the lipid portion of the composition. The cationic lipid can comprise varying mole percents of the lipid portion. Examples of cationic lipids include, without limitation, DODAC, DODAP, DODMA, DOTAP, DOTMA, DC-Chol, DMRIE, and DSDAC. Non-cationic lipids are also useful in formulating the lipid portion of the composition. The non-cationic lipid can comprise varying mole percents of the lipid portion. Examples of non-cationic lipids include, without limitation, phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

Moreover, the lipid-therapeutic nucleic acid particles of the present invention are serum-stable and, thus, not significantly degraded after exposure to a serum or nuclease assay that would significantly degrade free DNA. Suitable assays for measuring serum stability include a standard serum assay or a DNase assay (which are described in the Example section). Nuclease resistance/serum stability is a measure of the ability of the formulation to protect the therapeutic nucleic acid from nuclease digestion either in an in vitro assay or in circulation. The encapsulated particles of the present invention have greater nuclease resistance and serum stability than lipid-plasmid aggregates (also known as cationic complexes or lipoplexes), such as DOTMA/DOPE (LIPOFECTIN™) formulations.

In addition, the lipid-therapeutic nucleic acid particles of the present invention have a nucleic acid to lipid ratio that can be formulated at various levels. For use in the methods of this invention, the particles have a drug to lipid ratio of at least about 3 mg of nucleic acid per mmol of lipid, more preferably, at least about 14 mg of nucleic acid per mmol of lipid and, even more preferably, greater than about 25 mg of nucleic acid per mmol of lipid. The preferred particles, when prepared to an administration ready formulation, are about 60-80 mg nucleic acid per mmol lipid (i.e., they are "high ratio" formulations). The method used for making high ratio formulations can also be employed using reduced amounts of DNA to obtain lower ratio formulations. As used herein, "drug to lipid ratio" refers to the amount of therapeutic nucleic acid (i.e., the amount of nucleic acid that is encapsulated and that will not be rapidly degraded upon exposure to the blood) in a defined volume of preparation divided by the amount of lipid in the same volume. This may be determined on a mole per mole basis, on a weight per weight basis, or on a weight per mole basis. For final administration ready formulations, the drug to lipid ratio is calculated after dialysis, chromatography and/or nuclease digestion have been employed to remove as much of the externally associated therapeutic agent as possible. Drug to lipid ratio is a measure of potency of the formulation, although the highest possible drug to lipid ratio is not always the most potent formulation.

An alternative description of the lipid-nucleic acid particles of the present invention is "high efficiency" formulations that emphasizes the active loading process involved and contrasts with low efficiency or passive encapsulation. Passive encapsulation of nucleic acid in lipid particles, which is known in the art, achieves less than 15% encapsulation of therapeutic agent, and results in low ratio particles having less than 3 mg of nucleic acid per mmol of lipid. The preferred lipid/therapeutic nucleic acid particles of the present invention have an encapsulation efficiency of greater than about 30%. As used herein, "encapsulation efficiency" refers to absolute efficiency, i.e., the total amount of DNA added to the starting mixture that ends up in the administration competent formulation. Sometimes the relative efficiency is calculated, wherein the drug to lipid ratio of the starting mixture is divided by the drug to lipid ratio of the final, administration competent formulation. The amount of lipid lost during the formulation process may be calculated. Efficiency is a measure of the wastage and expense of the formulation.

Other beneficial features that flow from the use of the preferred particles of the present invention, such as low nonspecific toxicity, improved biodistribution, therapeutic efficacy and ease of manufacturing, will be apparent to those of skill in the art. It is possible to develop particles as described above by alternative methods of encapsulation. These methods may employ standard techniques for loading of liposomes that are well known for use with conventional drugs. These methods include freeze-thaw extrusion, dehydration/rehydration, reverse phase evaporation, and the like, some of which are disclosed in Monnard, et al., "Entrapment of nucleic acids in liposomes," *Biochim. Biophys. Acta.*, 1329:39-50 (1997). These methods are not high encapsulation efficiency formulations, nor high ratio formulations, but the instant disclosure suggests the utility of such particles in the use of gene therapy against distal tumor sites.

In addition to the lipids employed in the methods used above, there are a tremendous number of additional lipid and nonlipid components which can be used to enhance delivery or targeting of particles. Additional lipid components include, but are not limited to, lipids with neutral, anionic, cationic or zwitterionic headgroups, and the like. These standard components are set out in the art and in the patent applications referred to above which are incorporated herein by reference. Charged lipids that are particularly preferred with the invention are N,N-dioleyl-N,N-dimethylammonium chloride (DODAC), the subject of recently issued U.S. Pat. No. 5,753,613, incorporated herein by reference; and 1,2-Dioleoyl-3-dimethylammonium-propane (DODAP), the subject of U.S. patent application Ser. No. 08/856,374, the teachings of which are incorporated herein by reference.

In addition, cloaking agents or bilayer stabilizing compents can be used to reduce elimination by the host immune system. Such cloaking agents include, for example, polyamide oligomer-lipid conjugates, such as ATTA-lipids, disclosed in U.S. patent application Ser. No. 08/996,783, filed Feb. 2, 1998 and PEG-lipid conjugates (e.g., PEG-ceramides, PEG-phohspholipids, and PEG-diacylglycerols), some of which are disclosed in U.S. patent application Ser. Nos. 08/486,214, 08/316,407 and 08/485,608, the teachings of which are incorporated herein by reference. These components can also be targeting agents that encourage the lipid formulations to accumulate at the area of the disease or target site. In addition, these components can be compounds that improve features of the formulation, such as leakiness, longevity in circulation, reduction in toxicity, encapsulation efficiency, etc. Examples of these components and others that can usefully be included in the formulations of the invention are known to and used by those skilled in the art.

VII. Methods of Expressing a Nucleic Acid Encoding a Product of Interest

The expression cassettes encoding a product of interest can be expressed in a cell using the methods of the present invention. In one embodiment, the product of interest is expressed in a cell by introducing into the cell an expression cassette comprised of a RNA polymerase promoter operably linked to a nucleic acid encoding a product of interest. The cell is then contacted with a sRNAP. Methods for introducing nucleic acids into cells have been described above. The sRNAP can be produced by another cell or bacteria, purified and then contacted with the cell containing the product of interest expression cassette. In other embodiments, the sRNAP is expressed from a cell in the same cell culture medium that is in contact with the cell containing the product of interest expression cassette. The sRNAPs when contacted with a cell, are taken up by that cell into the cytoplasm. The sRNAP will then transcribe the expression cassette encoding the product of interest. If the product of interest is a pharmaceutical, such as insulin or EPO, then it can be purified and processed for human clinical use to treat diseases such as diabetes (insulin) and anemia (EPO). Products of interest such as a restriction endonuclease can also be produced to be used in molecular biology techniques that are useful for diagnosing diseases (e.g., RFLP, etc.). In a preferred embodiments the product of interest is expressed by introducing into the cell an expression cassette encoding the product of interest present on the same nucleic acid molecule as the secretable RNA polymerase expression cassette.

VIII. Methods of Treating Disease

In certain embodiments, the methods of the present invention involve treating a disease in a subject. Essentially any disease that can be treated that involves the delivery of a therapeutic product to a situs involved in the pathology of a disease. In certain embodiments, cancers can be treated using the methods of the present invention. Cancers include without limitation, cancers of the brain, lung, prostate, breast, bone, pancrease, liver, kidney, mouth, ears, nose, throat, skin, colon, and blood. In addition autoimmune diseases such as myasthenia gravis (MG), systemic lupus erythematosis (SLE), rheumatoid arthritis (RA), multiple sclerosis (MS), and insulin-dependent diabetes mellitus (IDDM), can be treated using the methods of the present invention. Also, diseases such as cardiovascular diseases (e.g., hypercholesterolemia, hypertension, congestive heart failure, atherosclerosis, etc.), cystic fibrosis, sickle cell anemia, hemophilia, infectious disease (viral disease (AIDS, Herpes, etc), bacterial (pneumonia, TB, etc), and inflammatory diseases.

The methods of treating these diseases involve administering a therapeutically effective amount of an expression cassette comprised of a RNA polymerase promoter operably linked to a nucleic acid encoding a therapeutic product; and administering a therapeutically effective amount of a secretable RNA polymerase, wherein the secretable RNA polymerase comprises a RNA polymerase and a secretion domain. The expression cassette encoding a therapeutic product and the secretable RNA polymerase expression cassette can be present on the same or different molecules, preferably on the same molecule. In other embodiments, the sRNAP can be delivered as a purified sRNAP.

In particularly preferred embodiments, a cancer is treated by administering a sRNAP and an expression cassette encoding a cytotoxic gene that can convert a prodrug into a toxic compound, which is a version of the GDEPT system. The sRNAP and the therapeutic product expression cassette can be delivered simultaneously or non-simultaneously, preferably on the same molecule. The prodrug is then delivered as the free drug or, alternatively, it can be in a lipid formulation. Usually, the expression cassette encoding the therapeutic product will be delivered with the sRNAP to the target cell in advance of the prodrug in order to allow synthesis of the suicide gene product prior to the arrival of the prodrug. Thus, using the compositions and methods of the invention, the therapeutic product is delivered to the cell to direct synthesis of the suicide gene product, the cell is thereby sensitized, the prodrug is delivered to the cell, and patient therapy, e.g., reduction of tumor size inflammation or infectious load and the like, is achieved.

Combinations of expression cassettes, sRNAPs that are useful for treating cancers can be assayed for their effects on cell growth. If the product of interest is a product that can be used to treat cancer or to inhibit the growth of a cell, then a variety of in vitro and in vivo assays can be used to assess whether the product of interest is effective, e.g., ability to grow on soft agar, changes in contact inhibition and density limitation of growth, changes in growth factor or serum dependence, changes in the level of tumor specific markers, changes in invasiveness into Matrigel, changes in tumor growth in vivo, such as in transgenic mice, etc.

A. Assays for Changes in Cell Growth by Expression of Product of Interest Constructs The following are assays that can be used to identify product of interest constructs which are capable of regulating cell proliferation and tumor suppression. Functional product of interest constructs identified by the following assays can then be used in gene therapy to inhibit abnormal cellular proliferation and transformation.

1. Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify product of interest constructs, which when expressed in host cells, inhibit abnormal cellular proliferation and transformation. Typically, transformed host cells (e.g., cells that grow on soft agar) are used in this assay. Expression of a tumor suppressor gene in these transformed host cells would reduce or eliminate the host cells' ability to grow in stirred suspension culture or suspended in semi-solid media, such as semi-solid or soft. This is because the host cells would regenerate anchorage dependence of normal cells, and therefore require a solid substrate to grow. Therefore, this assay can be used to identify product of interest constructs which function as a tumor suppressor. Once identified, such product of interest constructs can be used in gene therapy to inhibit abnormal cellular proliferation and transformation.

Techniques for soft agar growth or colony formation in suspension assays are described in Freshney, *Culture of Animal Cells a Manual of Basic Technique*, 3$^{rd}$ ed., Wiley-Liss, New York (1994), herein incorporated by reference. See also, the methods section of Garkavtsev et al. (1996), supra, herein incorporated by reference.

2. Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when transfected with tumor suppressor genes, regenerate a normal phenotype and become contact inhibited and would grow to a lower density.

Contact inhibition and density limitation of growth assays can be used to identify product of interest constructs which are capable of inhibiting abnormal proliferation and transformation in host cells. Typically, transformed host cells (e.g., cells that are not contact inhibited) are used in this assay. Expression of a tumor suppressor gene in these transformed host cells would result in cells which are contact inhibited and grow to a lower saturation density than the transformed cells. Therefore, this assay can be used to identify product of interest constructs which function as a tumor suppressor. Once identified, such product of interest constructs can be used in gene therapy to inhibit abnormal cellular proliferation and transformation.

In this assay, labeling index with [$^3$H]-thymidine at saturation density is a preferred method of measuring density limitation of growth. Transformed host cells are transfected with a product of interest construct and are grown for 24 hours at saturation density in non-limiting medium conditions. The percentage of cells labeling with [$^3$H]-thymidine is determined autoradiographically. See, Freshney (1994), supra. The host cells expressing a functional product of interest construct would give arise to a lower labeling index compared to control (e.g., transformed host cells transfected with a vector lacking an insert).

3. Growth Factor or Serum Dependence

Growth factor or serum dependence can be used as an assay to identify functional product of interest constructs. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When a tumor suppressor gene is transfected and expressed in these transformed cells, the cells would reacquire serum dependence and would release growth factors at a lower level. Therefore, this assay can be used to identify product of interest constructs which function as a tumor suppressor. Growth factor or serum dependence of transformed host cells which are transfected with a product of interest construct can be compared with that of control (e.g., transformed host cells which are transfected with a vector without insert). Host cells expressing a functional product of interest would exhibit an increase in growth factor and serum dependence compared to control.

4. Tumor-Specific Marker Levels

Tumor cells release an increased amount of certain factors (hereinafter "tumor-specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178-184 (1985)). Similarly, Tumor angiogenesis factor (TAF) is released at a higher level in tumor cells than their normal counterparts. See, e.g., Folkman, Angiogenesis and cancer, *Sem Cancer Biol.* (1992)).

Tumor-specific markers can be assayed for to identify product of interest constructs, which when expressed, decrease the level of release of these markers from host cells. Typically, transformed or tumorigenic host cells are used. Expression of a tumor suppressor gene in these host cells would reduce or eliminate the release of tumor-specific markers from these cells. Therefore, this assay can be used to identify product of interest constructs which function as a tumor suppressor.

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111-130 (1985).

5. Invasiveness into Matrigel

The degree of invasiveness into Matrigel or some other extracellular matrix constituent can be used as an assay to identify product of interest constructs which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Therefore, functional product of interest constructs can be identified by measuring changes in the level of invasiveness between the host cells before and after the introduction of product of interest constructs. If a product of interest construct functions as a tumor suppressor, its expression in tumorigenic host cells would decrease invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

6. Cell Cycle Analysis

Cell cycle analysis can be used to determine if a gene can suppress the growth of a cell. Briefly, cells are transfected with an expression cassette containing the gene of interest. If the gene encodes a protein or other gene product that can arrest or inhibit cell division then the gene is suppressing the growth of the cells. Cell division, or mitosis, consists of several successive phases in a eukaryotic cell (*Molecular Biology of the Cell*, 3d edition (Alberts et al., eds., 1994)). These phases, in order, are known as $G_1$, S, $G_2$ and M. DNA replication takes place during the S phase. The mitotic phase, where nuclear division takes place, is termed the M phase. The $G_1$ phase is the time between the M phase and the S phase. $G_2$ is the time between the end of the S phase and the beginning of the M phase. Cells can pause in $G_1$ and enter a specialized resting state known as $G_0$. Cells can remain in $G_0$ for days to years, until they resume the cell-cycle. Methods of analyzing the phase of the cell-cycle are known in the art and include methods that involve determining if the cell is replicating DNA (e.g., [$H^3$]-thymidine incorporation assays). Alternatively, methods are known in the art for measuring the DNA content of a cell, which doubles during the S phase. FACS (Fluorescent activated cell sorting) analysis can be used to determine the percentage of a population of cells in a particular stage of the cell-cycle (see generally, Alberts et al., supra; see also van den Heuvel and Harlow, (1993) *Science* 262: 2050-2054). The cells are incubated with a dye that fluoresces (e.g., propidium iodide) when it binds to the DNA of the cell. Thus, the amount of fluorescence of a cell is proportional to the DNA content of a cell. Cells that are in $G_1$ or $G_0$ ($G_1/G_0$) have an unreplicated complement of DNA and are deemed to have 1 arbitrary unit of DNA in the cell. Those cells that have fully replicated, i.e., have doubled their DNA content, are deemed to have 2 arbitrary units of DNA in the cell and are in the $G_2$ or M phase ($G_2/M$) of the cell cycle. Cells with an amount of DNA that is between 1 and 2 arbitrary units are in S phase.

The effect of a protein of interest on the cell cycle can be determined by transfecting cells with DNA encoding the protein of interest and analyzing its effect on the cell cycle through flow cytometry in a FACS. The cells are co-transfected with a vector encoding a marker to identify and analyze those cells that are actually transfected. Such markers can include the B cell surface marker CD20 (van de Heuvel and Harlow, supra) or a farnesylated green fluorescent protein (GFP-F) (Jiang and Hunter, (1998) *Biotechniques*, 24(3): 349-50, 352, 354).

For example, the percentage of cells in a particular stage of the cell-cycle can be determined using the method of Jiang and Hunter, (1998) supra. Briefly, a population of cells are transfected with a vector encoding a product of interest and a vector encoding a green fluorescent protein (GFP) with a farnesylation signal sequence from c-Ha-Ras. The farnesylation signal sequence is farnesylated in the cell, which targets the GFP molecule to the plasma membrane. Vectors encoding farnesylated GFP are commercially available (e.g., pEGFP-F from Clontech).

After transfection, the cells are suspended in buffer containing the DNA intercalator propidium iodide. Propidium iodide will fluoresce when it is bound to DNA. Thus, the amount of fluorescence observed from propidium iodide in a FACS flow cytometer is an indication of the DNA content of a cell. The percentages of cells in each cell cycle can be calculated using computer programs, e.g., the ModFit program (Becton-Dickinson). The cell cycle stage of the cell was analyzed after gating cells by GFP fluorescence using FACscan. If the gene encodes a tumor suppressor, the percentage of cells that enter S phase would be decreased, as the cells are arrested in the $G_0/G_1$ phase. Therefore, the percentage of cells that are $G_0/G_1$ phase would be increased.

IX. Administration-Ready Pharmaceutical Preparations

Generally, when administered intravenously, the nucleic acid and/or the prodrug formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration. Carriers may also be employed when delivering the vector or prodrug formulations by other parenteral methods known in the art, such as subcutaneous, intratumoral or intramuscular injection, inhalation, and the like.

When preparing pharmaceutical preparations of the lipid/therapeutic nucleic acid particles of the invention, it is preferable to use quantities of the particles which have been purified to reduce or eliminate empty particles or particles with nucleic acid associated with the external surface.

A. Modes of Administration

The nucleic acids, sRNAPs, compounds, and compositions of the present invention can be delivered to treat disease in a subject using methods and modes of administration known to those of skill in the art. Modes of administration include, intra-cranial, ip, im, iv, oral, topical, etc. In certain embodiments, the sRNAP can be delivered to the subject at a site distal to a site where the product of interest is administered due to the translocation properties of the sRNAP. In other embodiments, the therapeutic product also has a secretion domain and can be cross the blood-brain barrier. In certain embodiments, where a cancer is being treated, the nucleic acids, sRNAPs, compounds, and/or compositions can be injected, for example, intravenously into blood veins feeding the tumor mass, or directly into the tumor (e.g., intratumoral injection).

EXAMPLES

The following examples are offered to illustrate, but not to limit the claimed invention.

Example 1

In Vitro Transcription and Translation of Secretable RNAP

A secretable RNAP expression cassette is added to an expression cassette encoding a reporter gene or product of interest and a RNA polymerase. Reporter gene activity is measured or the product of interest is detected. The reporter gene or product of interest is expressed if the RNAP polymerase transcribes the secretable RNAP expression cassette into mRNA. The secretable RNAP then transcribes the expression cassette encoding the reporter gene or the product of interest.

Figure 4:
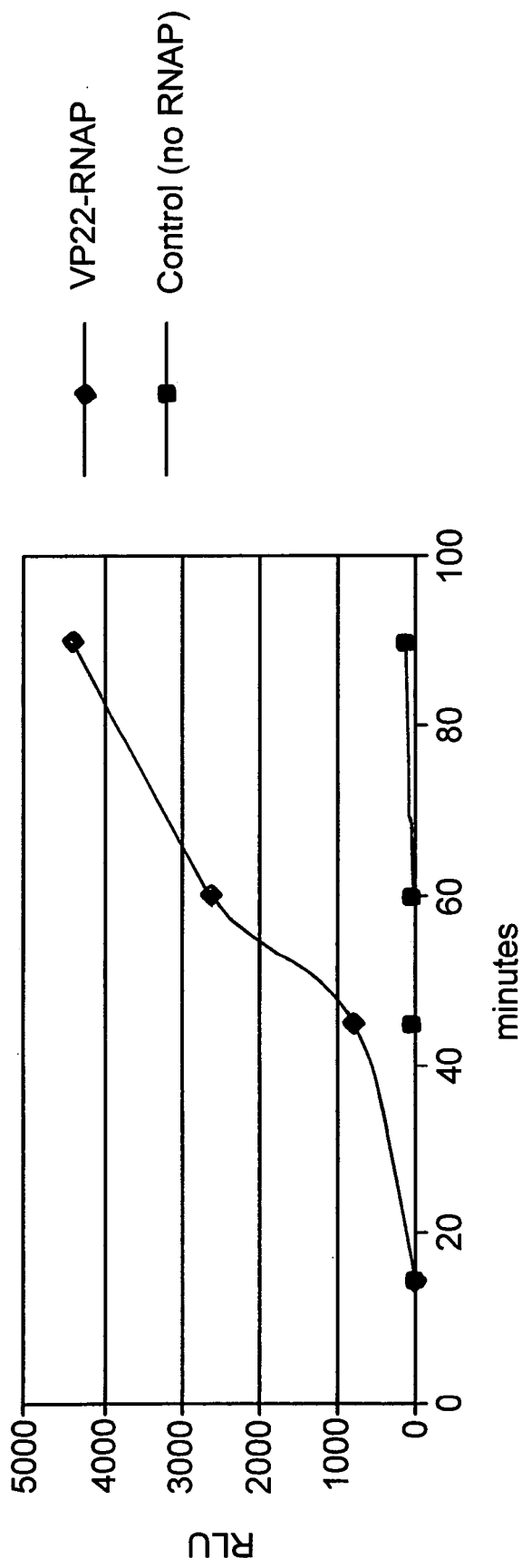
FIG. 4 illustrates in vitro transcription and translation of VP22-RNAP. 500 ng of a SP6-VP22-T7-RNAP (VP22: SEQ ID NO:21) construct was added to 250 ng of a T7-luciferase construct and 1 μl of SP6 RNA polymerase. Luciferase activity was measured over time.

500 ng of a SP6-VP22-T7-RNAP (VP22: SEQ ID NO:21) construct was added to 250 ng of a T7-luciferase construct and 1 µl of SP6 RNA polymerase. Luciferase activity was measured over time. The results are shown in FIG. 4.

Figure 5:
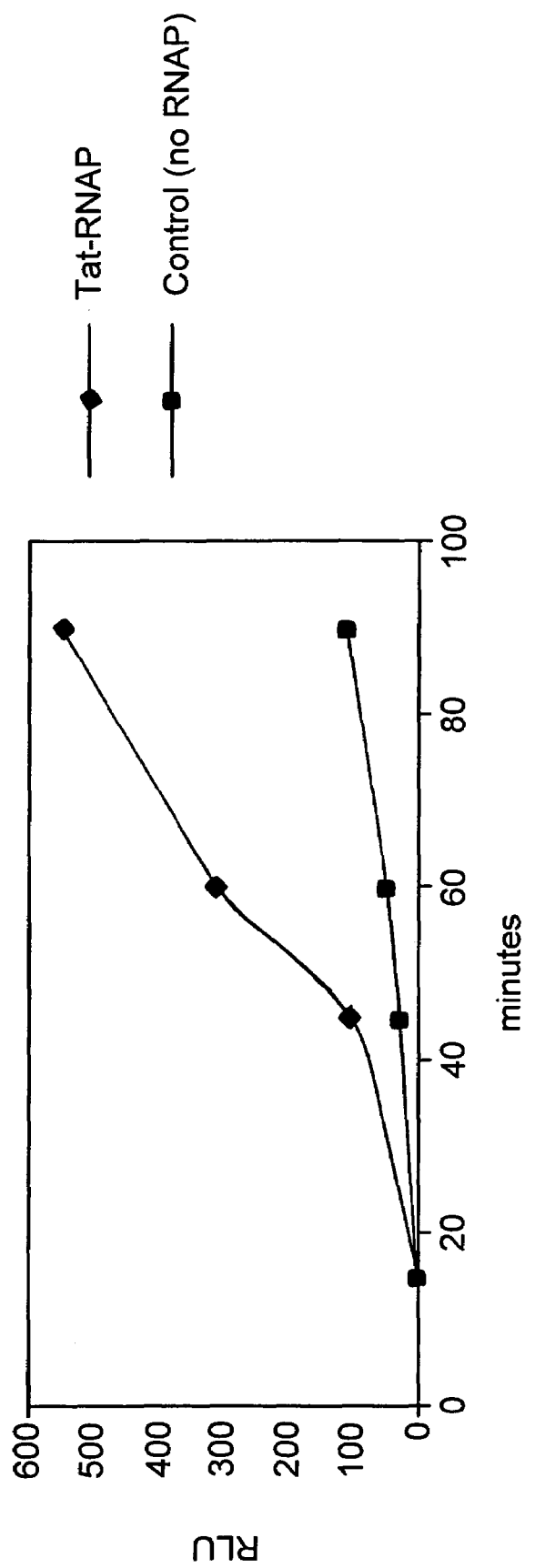
FIG. 5 illustrates in vitro transcription and translation of Tat-RNAP. 500 ng of a SP6-Tat-T7-RNAP (Tat: SEQ ID NO: 1) construct was added to 250 ng of a T7-luciferase construct and 1 μl of SP6 RNA polymerase. Luciferase activity was measured over time.

500 ng of a SP6-Tat-T7-RNAP (Tat: SEQ ID NO:1) construct was added to 250 ng of a T7-luciferase construct and 1 µl of SP6 RNA polymerase. Luciferase activity was measured over time. The results are shown in FIG. 5.

Example 2

Transfection of Cells with Secretable RNAP

Cells are transfected with an expression cassette encoding a reporter gene or a product of interest and an expression cassette encoding a secretable RNA polymerase. Transfection may be simultaneous or sequential. The expression cassettes may be naked nucleic acid or may be encapsulated in a liposome. Cells are harvested at several time points after transfection. Reporter gene activity is measured or the product of interest is detected.

Figure 2:
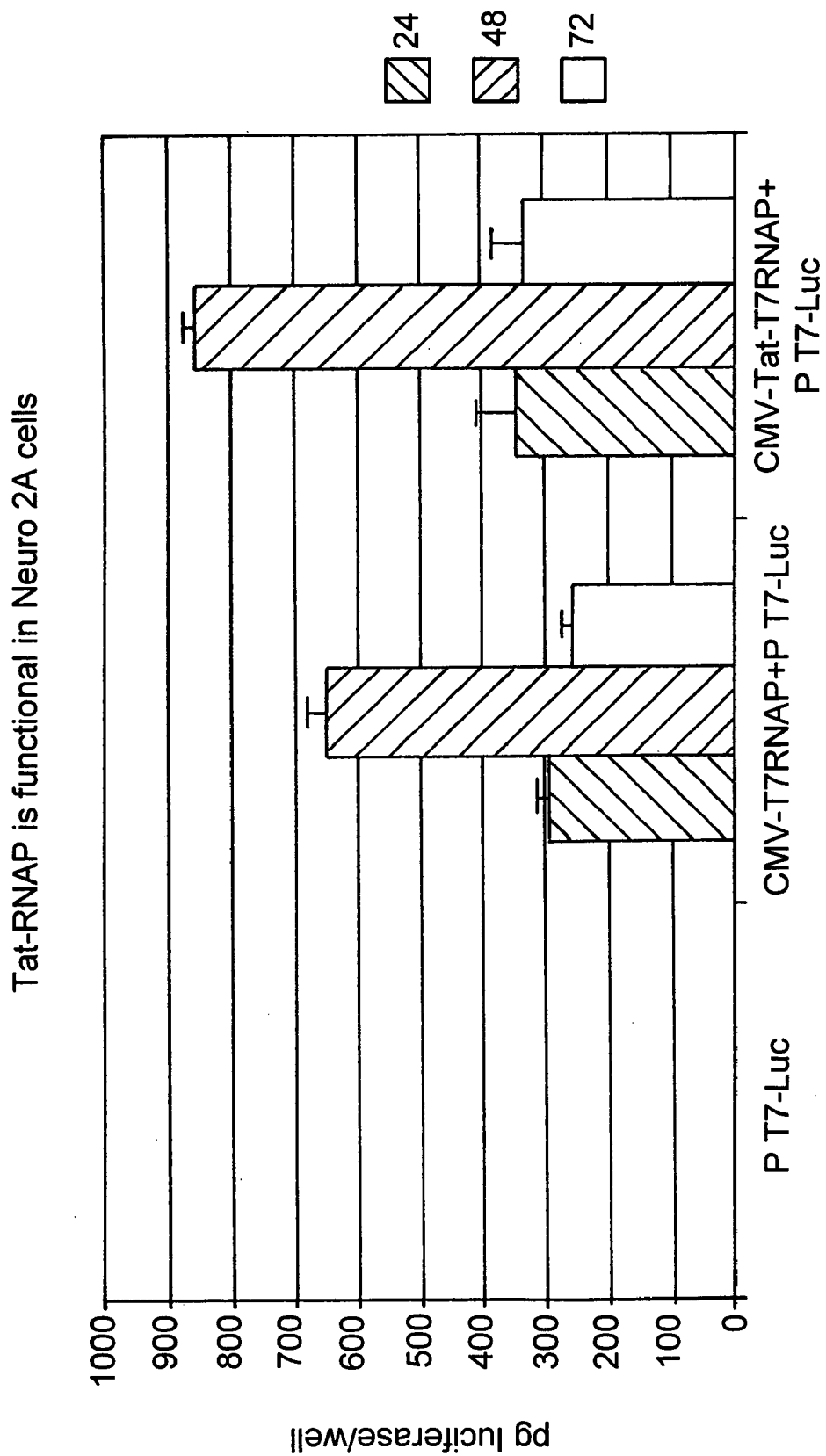
FIG. 2 illustrates in vitro transfection of Neuro 2A cells with Tat-RNAP (Tat: SEQ ID NO:1). Neuro 2A cells were transfected with T7-luciferase and CMV-Tat-RNAP constructs in DOPE:DODAC (50:50) large unilamellar vesicles (LUVs). Cells were harvested 24, 48, and 72 hours after transfection and luciferase activity was measured.

Neuro 2A cells were transfected with T7-luciferase and CMV-Tat-RNAP (Tat: SEQ ID NO: 1) constructs in DOPE; DODAC (50:50) large unilamellar vesicles (LUVs). Cells were harvested 24, 48, and 72 hours after transfection and luciferase activity was measured. The results are shown in FIG. 2.

Figure 3:
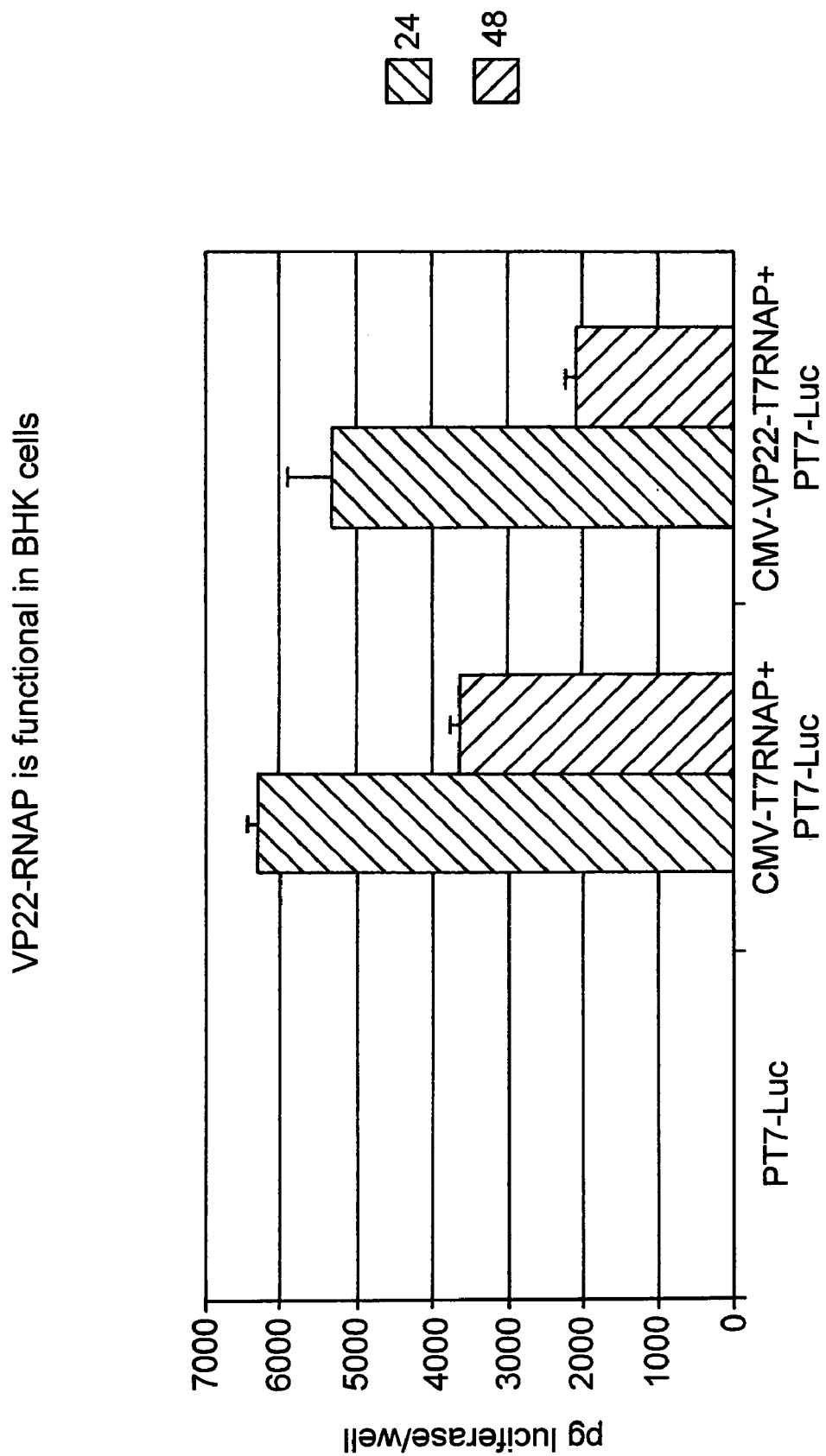
FIG. 3 illustrates in vitro transfection of baby hamster kidney (BHK) cells with VP22-RNAP (VP22: SEQ ID NO:21). BHK cells were transfected with T7-luciferase and CMV-VP22-RNAP constructs in DOPE:DODAC (50:50) large unilamellar vesicles (LUVs). Cells were harvested 24, 48, and 72 hours after transfection and luciferase activity was measured.

BHK cells were transfected with T7-luciferase and CMV-VP22-RNAP (VP22: SEQ ID NO:21) constructs in DOPE; DODAC (50:50) large unilamellar vesicles (LUVs). Cells were harvested 24, 48, and 72 hours after transfection and luciferase activity was measured. The results are shown in FIG. 3.

Figure 6:
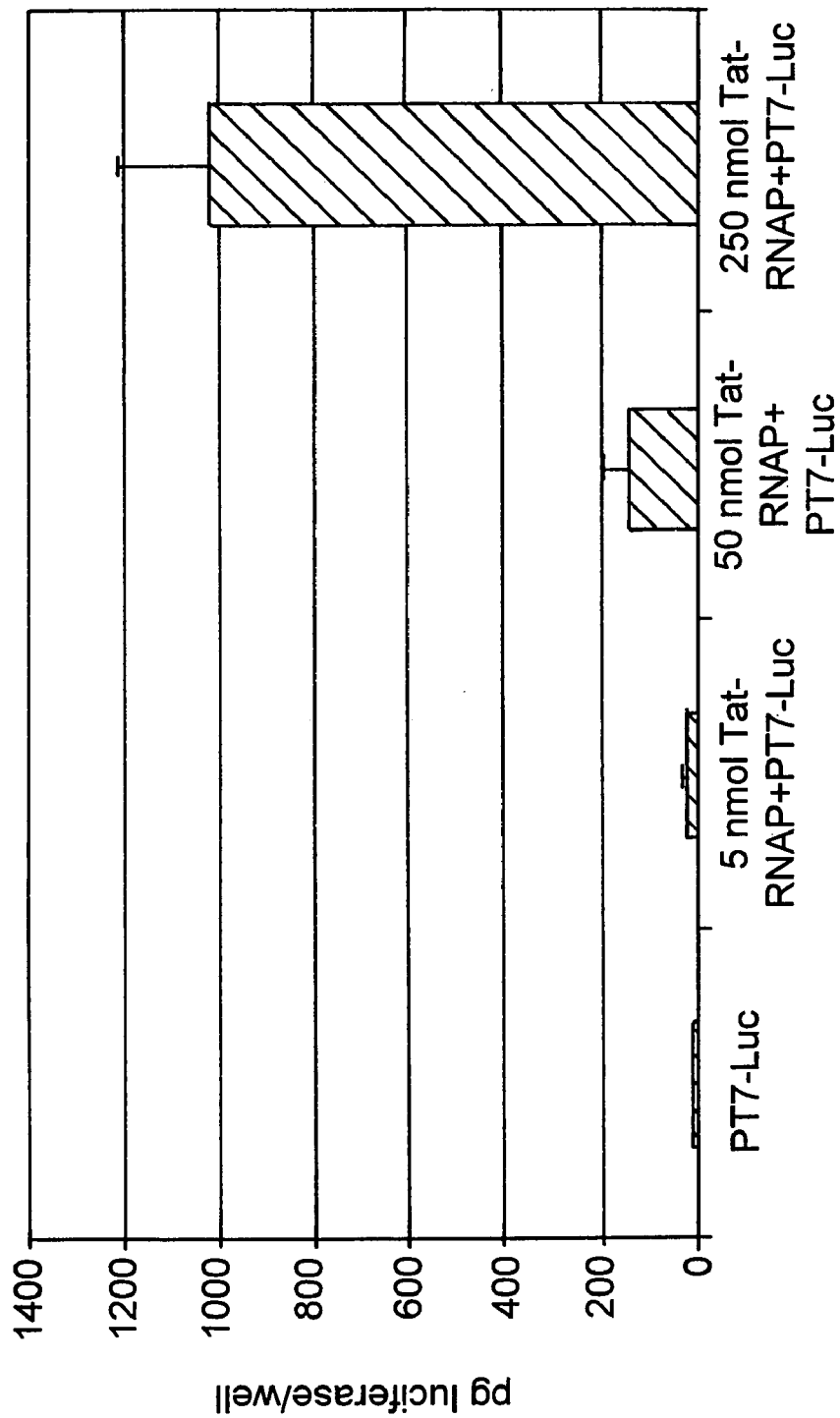
FIG. 6 illustrates in vitro transfection and translation of Tat-RNAP and luciferase. BHK cells were transfected with 5, 50, or 250 mmol of purified Tat-RNAP (Tat: SEQ ID NO: 1) for 4 hours, washed with PBS, and transfected with 0.75 μg of a T7-luciferase construct.

BHK cells were transfected with 5, 50, or 250 mmol of purified Tat-RNAP (Tat: SEQ ID NO: 1) for 4 hours, washed with PBS, and transfected with 0.75 µg of a T7-luciferase construct. Luciferase activity was measured. The results are shown in FIG. 6.

Example 3

Transfection of Cells with Secretable RNAP

Cells are transfected with an expression cassette encoding a reporter gene or an expression cassette encoding a product of interest and a secretable RNA polymerase. The expression cassette may be naked nucleic acid or may be encapsulated in a liposome. at suitable times after transfection, cell populations are mixed. Cells are harvested at several time points after mixing. Reporter gene activity is measured or the product of interest is detected.

Figure 7:
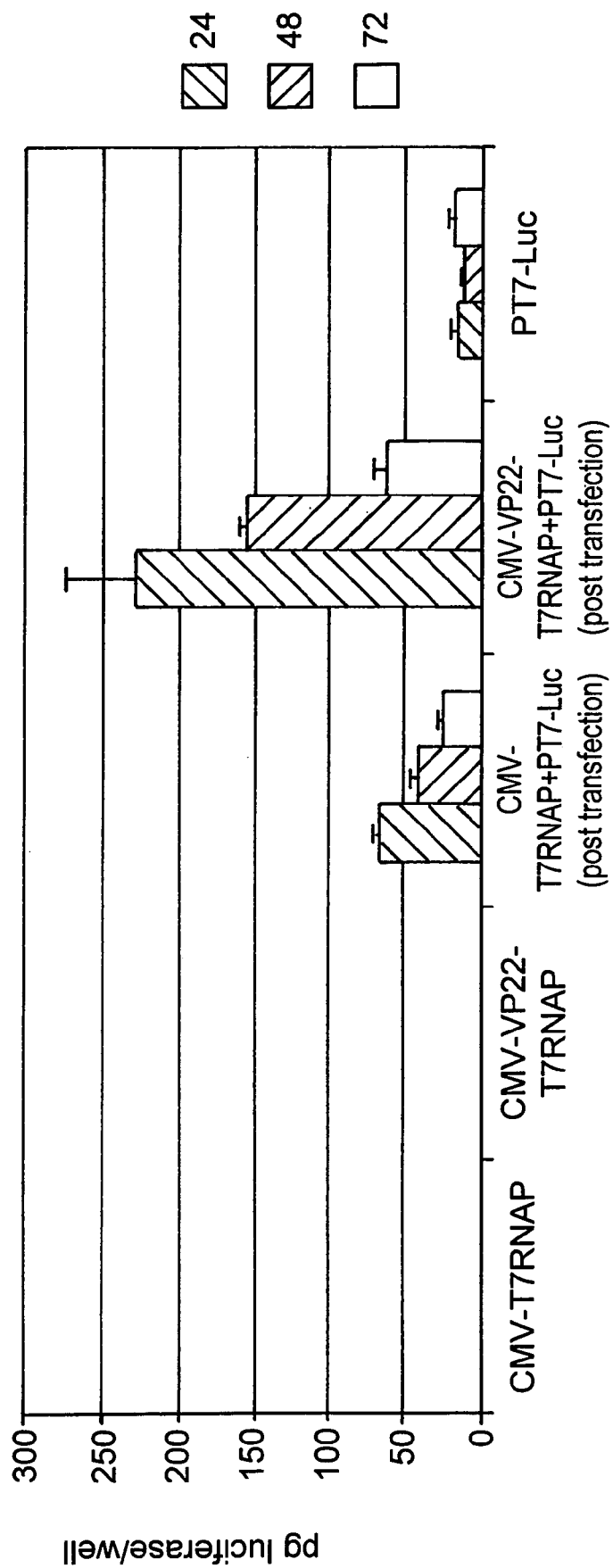
FIG. 7 illustrates in vitro transfection of VP22-RNAP. BHK cells were transfected with 1 μg of a CMV-T7 RNAP construct or a CMV-VP22-T7RNAP construct (VP22: SEQ ID NO:21). Four hours after transfection, the BHK cells were trypsinized and added to BHK cells transfected with T7-luciferase. Cells were harvested 24, 48, or 72 hours after mixing of the cell populations and luciferase activity was measured.

BHK cells were transfected with 1 µg of a CMV-T7 RNAP construct or a CMV-VP22-T7RNAP construct (VP22: SEQ ID NO:21). Four hours after transfection, the BHK cells were trypsinized and added to BHK cells transfected with T7-luciferase. Cells were harvested 24, 48, or 72 hours after mixing of the cell populations and luciferase activity was measured. The results are shown in FIG. 7.

Example 4

DNAse I Assay

To evaluate the protective effect of the lipid on nucleic acids, the nucleic acid-lipid particle is incubated with DNase I at a concentration where the nucleic acid alone is susceptible to degradation at 37° C. for 10 minutes. The reaction is stopped by the addition of 25 mM EDTA and the samples are extracted using methods known in the art, in the presence of 150 mM NaCl. (See, e.g., Bligh and Dyer, *Ca. J. Biochem. Physiol.* 37:91 (1959)). The DNA is precipitated with $\frac{1}{10}^{th}$ volume of 3 M sodium acetate (pH 5.2) and 2.5 volumes of 95% EtOH and recovered by centrifugation at 14,000×G for 30 minutes at 4° C. The DNA pellet is resuspended in sterile distilled water and subjected to electrophoresis on an 0.8% agarose gel.

Example 5

Serum Stability Assay

To evaluate the serum stability of the nucleic acid-lipid particles, an aliquot of the nucleic acid-lipid particle is incubated in mouse serum 37° C. for 30 minutes. The incubation mixture is eluted in HBS on a Sepharose CL-4B column. Comigration of the nucleic acid and lipid in the void volume suggests that no nucleic acid degradation has occurred.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A secretable RNA polymerase expression cassette comprising:
   (a) a eukaryotic promoter and a first RNA polymerase promoter operably linked to a nucleic acid encoding a secretable RNA polymerase (sRNAP) comprising a RNA polymerase and a secretion domain; and
   (b) a second RNA polymerase promoter operably linked to a nucleic acid encoding a product of interest, wherein the sRNAP enters the cytoplasm of a cell and carries out template dependent synthesis of RNA.

2. The expression cassette of claim 1, wherein said RNA polymerase is a non-host RNA polymerase.

3. The expression cassette of claim 1, wherein said RNA polymerase is a member selected from the group of: a phagemid RNA polymerase, a prokaryotic RNA polymerase, an archaebacterial RNA polymerase, a plant RNA polymerase, a fungal RNA polymerase, a eukaryotic RNA polymerase, a viral RNA polymerase, mitochondrial RNA polymerase, and a chloroplast RNA polymerase.

4. The expression cassette of claim 3, wherein said phagemid RNA polymerase is a member selected from the group consisting of: a SP6 RNA Polymerase, a T7 RNA Polymerase, a K11 RNA Polymerase, and a T3 RNA Polymerase.

5. The expression cassette of claim 1, wherein said product of interest is a member selected from the group consisting of: a protein, a nucleic acid, an antisense nucleic acid, ribozymes, tRNA, snRNA, and an antigen.

6. The expression cassette of claim 1, wherein said product of interest encodes a protein selected from the group consisting of:
   a herpes simplex virus thymidine kinase (HSV-TK), a cytosine deaminase, a xanthine-guaninephosphoribosyl transferase, a purine nucleoside phosphorylase, a carboxylesterase, a deoxycytidine kinase, a nitroreductase, a thyrnidine phosphorylase, and a cytochrome P450 2B1.

7. The expression cassette of claim 1, wherein said product of interest encodes a protein selected from the group consisting of: p53, a retinoblastoma susceptibility gene product (RB1), a calmodulin-dependent serine threonine (DAP kinase), p16, a protein from an alternative reading frame of p16 (ARF), an adenomatous polyposis coli gene product (APC), neurofibromin, a phosphatase and tensin homologue deleted from chromosome 10 (PTEN), a Wilms= tumor gene product (WT1), a neurofibromatosis type 1 gene product (NF1), and a von Hippel-Lindau tumor suppressor gene product (VHL).

8. The expression cassette of claim 1, wherein said product of interest encodes a protein selected from the group consisting of: angiostatin, endostatin, and vascular endothelial growth factor (VEGF)-R2.

9. The expression cassette of claim 1, wherein said product of interest encodes apoptin.

10. The expression cassette of claim 1, wherein said product of interest encodes a protein selected from the group consisting of: IL-2, IL-3, IL-4, IL-6, IL-7, IL-10, IL-12, IL-15, IFN-α, IFN-β, IFN-γ, TNF-α, GM-CSF, G-CSF, and Fms-like tyrosine kinase 3 (Flt3)-Ligand.

11. The expression cassette of claim 1, wherein said product of interest is a protein selected from the group consisting of: a restriction endonuclease, a single chain antibody, a peptide hormone, erythropoietin (EPO), and single-chain insulin.

12. The expression cassette of claim 1, wherein said eukaryotic promoter is a member selected from a group consisting of: a cytomegalovirus promoter, a von Willebrand factor (vWf) promoter, a Clara cell secretory protein (CCSP/UG) promoter, an osteoblast-specific osteocalcin promoter, an albumin promoter, a muscle creatine kinase (MCK) promoter, a mucin-1 (Muc-1) promoter, a carcinoembryonic antigen (CEA) promoter, a prostate specific antigen (PSA) promoter, an epidermal growth factor receptor (HER-2) promoter, a Myc promoter, a L-plastin promoter, an alpha-fetoprotein (AFP) promoter, a hypoxia-responsive element (HIRE) promoter, an early growth response (egr-1) promoter, a multidrug resistance (mdr-1) promoter, a heat shock protein 70 (hsp70) promoter, a tetracycline induced promoter, a simian virus 40 (SV40) promoter, an alcohol dehydrogenase (ADH1) promoter, a GAL4 promoter, a LexA promoter, a rous sarcoma virus (RSV) promoter, a human imniunodeficiency virus (HIV) promoter, and a simian foamy virus (SFV) promoter.

13. A lipid-nucleic acid composition comprising:
a nucleic acid-lipid particle comprising a lipid portion and a nucleic acid portion,
wherein said nucleic acid portion comprises a secretable RNA polymerase expression cassette comprising:
(a) a eukaryotic promoter and a first RNA polymerase promoter operably linked to a nucleic acid encoding a secretable RNA polymerase comprising a RNA polymerase and a secretion domain; and
(b) a second RNA polymerase promoter operably linked to a nucleic acid encoding a product of interest.

14. The nucleic acid of claim 13, wherein a RNA polymerase promoter is operably linked to said nucleic acid encoding a secretable RNA polymerase.

15. The lipid-nucleic acid composition of claim 13, wherein said nucleic acid-lipid particle is a serum-stable nucleic acid-lipid particle comprising a nucleic acid fuily encapsulated within said lipid portion.

16. The lipid-nucleic acid composition of claim 13, wherein said lipid portion comprises a protonatable lipid having a pKa in a range of about 4 to about 11.

17. The lipid-nucleic acid composition of claim 13, wherein said lipid portion comprises a cationic lipid.

18. The lipid-nucleic acid composition of claim 17, wherein said cationic lipid is a member selected from the group consisting of DODAC, DODAP, DODMA, DOTAP, DOTMA, DC-Chol, DMRIE, and DSDAC.

19. The expression cassette of claim 1, wherein said secretion domain is an importation competent signal peptide.

20. The expression cassette of claim 1, wherein said secretion domain is a protein transduction domain.

21. The expression cassette of claim 20, wherein said protein transduction domain is a TAT polypeptide.

22. The expression cassette of claim 21, wherein said TAT polypeptide comprises the amino acid sequence $X_1$-$X_2$-$X_3$-$X_4$-$X_5$-$X_6$-$X_7$-$X_8$-$X_9$-Arg-$X_{10}$, wherein $X_1$ is Tyr or Ala;

$X_2$ is Gly or Ala;

$X_3$, $X_6$, $X_7$, $X_9$ and $X_{10}$ are Arg or Ala; and $X_8$ is Gln, Arg or Ala.

23. The expression cassette of claim 22, wherein said TAT polypeptide comprises SEQ ID NO:1.

24. The lipid-nucleic acid composition of claim 13, wherein said secretion domain is an importation competent signal peptide.

25. The lipid-nucleic acid composition of claim 13, wherein said secretion domain is a protein transduction domain.

26. The lipid-nucleic acid composition of claim 25, wherein said protein transduction domain is a TAT polypeptide.

27. The lipid-nucleic acid composition of claim 26, wherein said TAT polypeptide comprises the amino acid sequence $X_1$-$X_2$-$X_3$-$X_4$-$X_5$-$X_6$-$X_7$-$X_8$-$X_9$-Arg-$X_{10}$, wherein $X_1$ is Tyr or Ala;

$X_2$ is Gly or Ala;

$X_3$, $X_6$, $X_7$, $X_9$ and $X_{10}$ are Arg or Ala; and $X_8$ is Gln, Arg or Ala.

28. The lipid-nucleic acid composition of claim 27, wherein said TAT polypeptide comprises SEQ ID NO:1.

29. The expression cassette of claim 1, wherein the RNA polymerase is a T7 RNA polymerase.

30. The lipid-nucleic acid composition of claim 13, wherein the RNA polymerase is a T7 RNA polymerase.

* * * * *